United States Patent [19]
Nikoonahad et al.

[11] Patent Number: 5,825,482
[45] Date of Patent: Oct. 20, 1998

[54] SURFACE INSPECTION SYSTEM WITH MISREGISTRATION ERROR CORRECTION AND ADAPTIVE ILLUMINATION

[75] Inventors: Mehrdad Nikoonahad, Atherton; Charles E. Wayman, San Jose, both of Calif.

[73] Assignee: Kla-Tencor Corporation, San Jose, Calif.

[21] Appl. No.: 827,859

[22] Filed: Apr. 9, 1997

Related U.S. Application Data

[63] Continuation-in-part of Ser. No. 536,862, Sep. 29, 1995.
[51] Int. Cl.$^6$ ..................................................... G01N 21/00
[52] U.S. Cl. .......................... 356/237; 356/338; 356/445; 356/448
[58] Field of Search ..................................... 356/237, 338, 356/445, 448, 394

[56] References Cited

U.S. PATENT DOCUMENTS

| | | |
|---|---|---|
| 3,851,951 | 12/1974 | Eveleth . |
| 4,391,524 | 7/1983 | Steigmeier et al. . |
| 4,405,238 | 9/1983 | Grobman et al. . |
| 4,441,124 | 4/1984 | Heebner et al. . |
| 4,532,650 | 7/1985 | Wihl et al. . |
| 4,556,290 | 12/1985 | Roulot . |
| 4,579,455 | 4/1986 | Levy et al. . |
| 4,589,773 | 5/1986 | Ido et al. . |
| 4,601,576 | 7/1986 | Galbraith . |
| 4,614,427 | 9/1986 | Koizumi et al. . |
| 4,650,983 | 3/1987 | Suwa . |
| 4,728,190 | 3/1988 | Knollenberg . |
| 4,748,333 | 5/1988 | Mizutani et al. . |
| 4,786,815 | 11/1988 | Walker et al. . |
| 4,805,123 | 2/1989 | Specht et al. . |
| 4,844,617 | 7/1989 | Kelderman et al. . |
| 4,864,123 | 9/1989 | Mizutani et al. . |
| 4,864,147 | 9/1989 | Ikari et al. . |
| 4,889,998 | 12/1989 | Hayano et al. . |
| 4,891,526 | 1/1990 | Reeds . |
| 4,898,471 | 2/1990 | Stonestrom et al. . |
| 4,912,487 | 3/1990 | Porter et al. . |

(List continued on next page.)

OTHER PUBLICATIONS

Carmel et al., "New Directions in Process Control," *SPIE*, vol. 2196, pp. 332–340.

Dralla et al., "Inspection of Patterned Wafers: 0.35 μm Design Rules and Beyond," presented at Semicon, Kansai, Japan, Jun. 15–17, 1994.

Gottlieb, "Acoustooptic Scanners and Modulators," publication of Westinghouse Electric Corporation, pp. 615–685.

Clark et al., "Dynamic performance of a scanning X–Y stage for automted electron–beam inspection," *J. Vac. Sci., Techno.*, B 10(6), Nov./Dec. 1992, pp. 2638–2642.

Alumont et al., "Dual sensor technology for high–speed detection of 0.1 micron defects," *SPIE*, vol. 1926, Integrated Circuit Metrology, Inspection, and Process Control VII, 1993, pp. 1–12.

Warner et al., "Reviewing Angle–Resolved Methods for Improved Surface Particle Detection," *Microcontamination*, Sep./Oct. 1993, pp. 35–39 and 109.

*Primary Examiner*—Frank G. Font
*Assistant Examiner*—Reginald A. Ratliff
*Attorney, Agent, or Firm*—Majestic, Parsons, Siebert & Hsue

[57] ABSTRACT

An optical surface inspection system is designed to correct for misregistration errors. A reference vector of data samples is obtained by computing an average of adjacent data sample vectors. A comparison of the data samples in a current vector being processed to data samples that may be offset from such current vector along the direction of the current vector enables the detection and correction of misregistration errors. Alternatively, a target array of data samples is compared to a reference array of data samples collected from a different portion of the surface with various offsets for detection and correction of misregistration errors. The intensity of the reflection from the inspection beam may be monitored to vary the intensity of the inspection beam so as to reduce the dynamic range of background scattering.

70 Claims, 21 Drawing Sheets

U.S. PATENT DOCUMENTS

| | | |
|---|---|---|
| 4,926,489 | 5/1990 | Danielson et al. . |
| 4,936,676 | 6/1990 | Stauffer . |
| 4,966,455 | 10/1990 | Avni et al. . |
| 4,966,457 | 10/1990 | Hayano et al. . |
| 5,004,929 | 4/1991 | Kakinoki et al. . |
| 5,027,132 | 6/1991 | Manns et al. . |
| 5,030,008 | 7/1991 | Scott et al. . |
| 5,122,898 | 6/1992 | Picault . |
| 5,162,642 | 11/1992 | Akamatsu et al. . |
| 5,166,516 | 11/1992 | Kajimura . |
| 5,272,517 | 12/1993 | Tokura . |
| 5,317,380 | 5/1994 | Allemand . |
| 5,363,187 | 11/1994 | Hagiwara et al. . |
| 5,530,550 | 6/1996 | Nikoonahad et al. . |
| 5,619,429 | 4/1997 | Aloni et al. . |
| 5,619,588 | 4/1997 | Yolles et al. . |

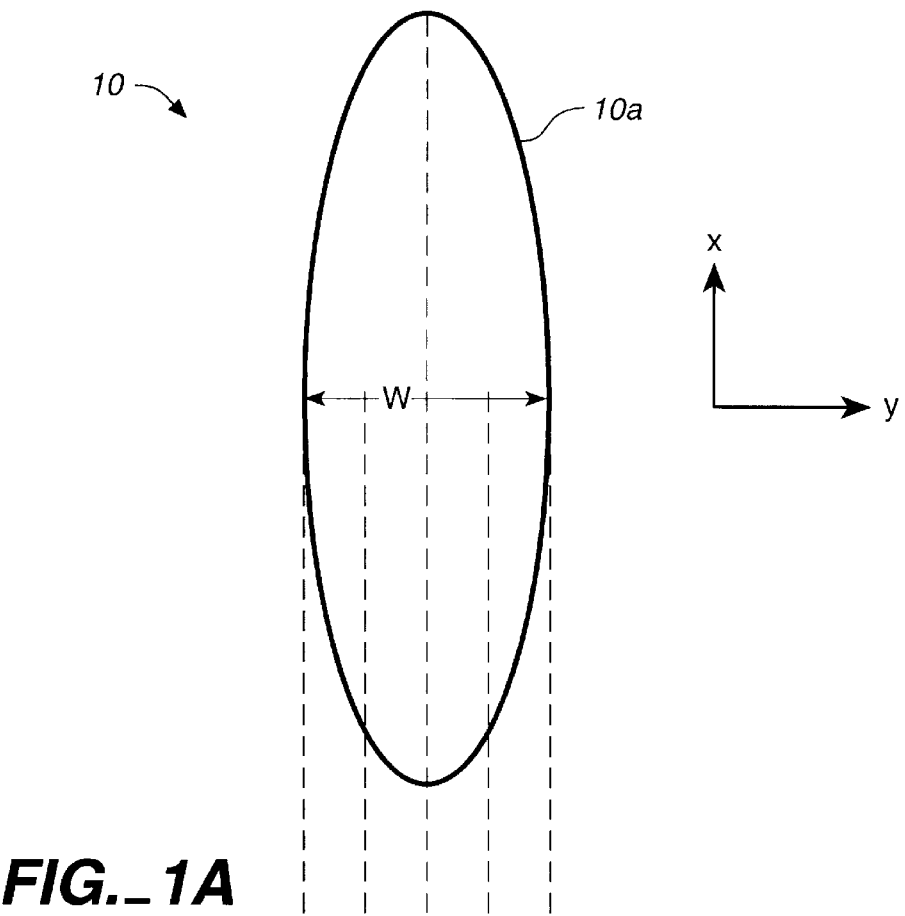
FIG._1A
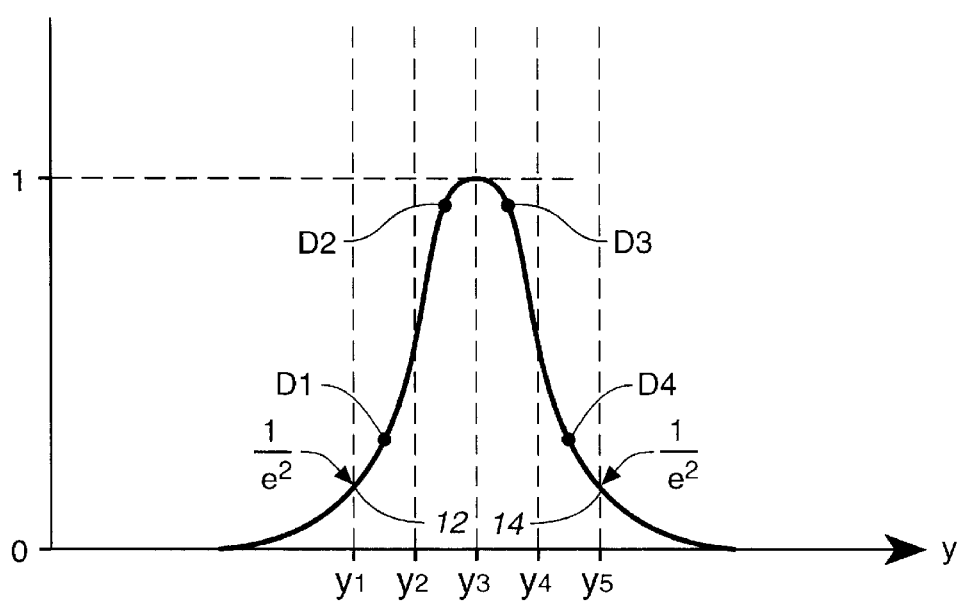
FIG._1B

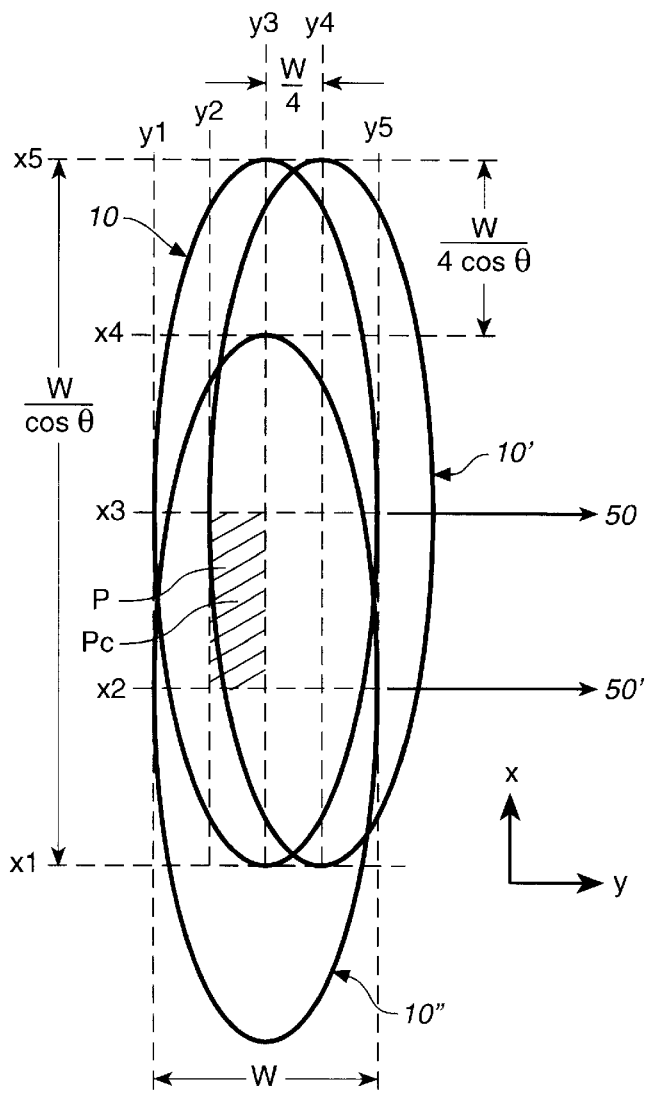

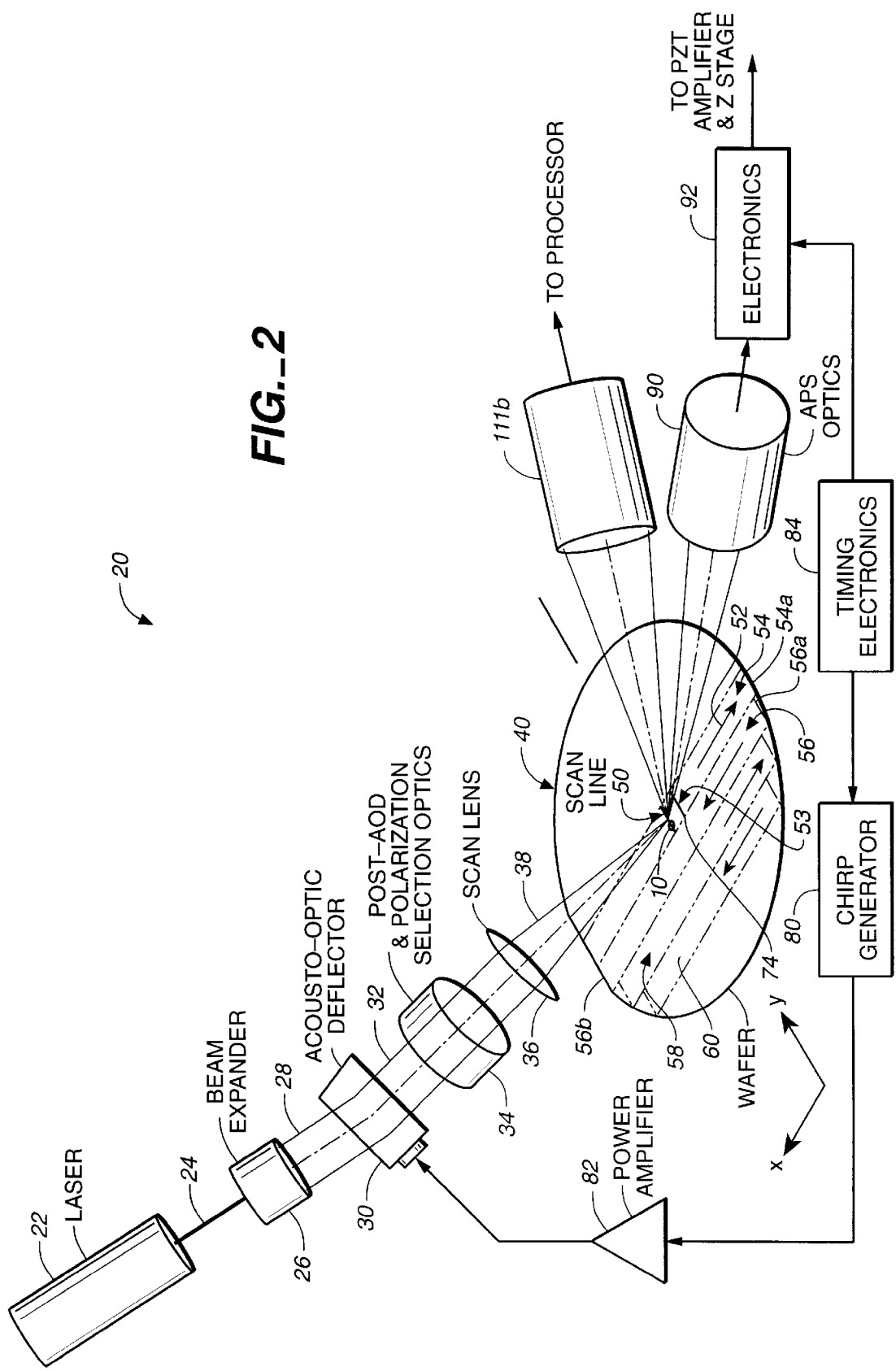

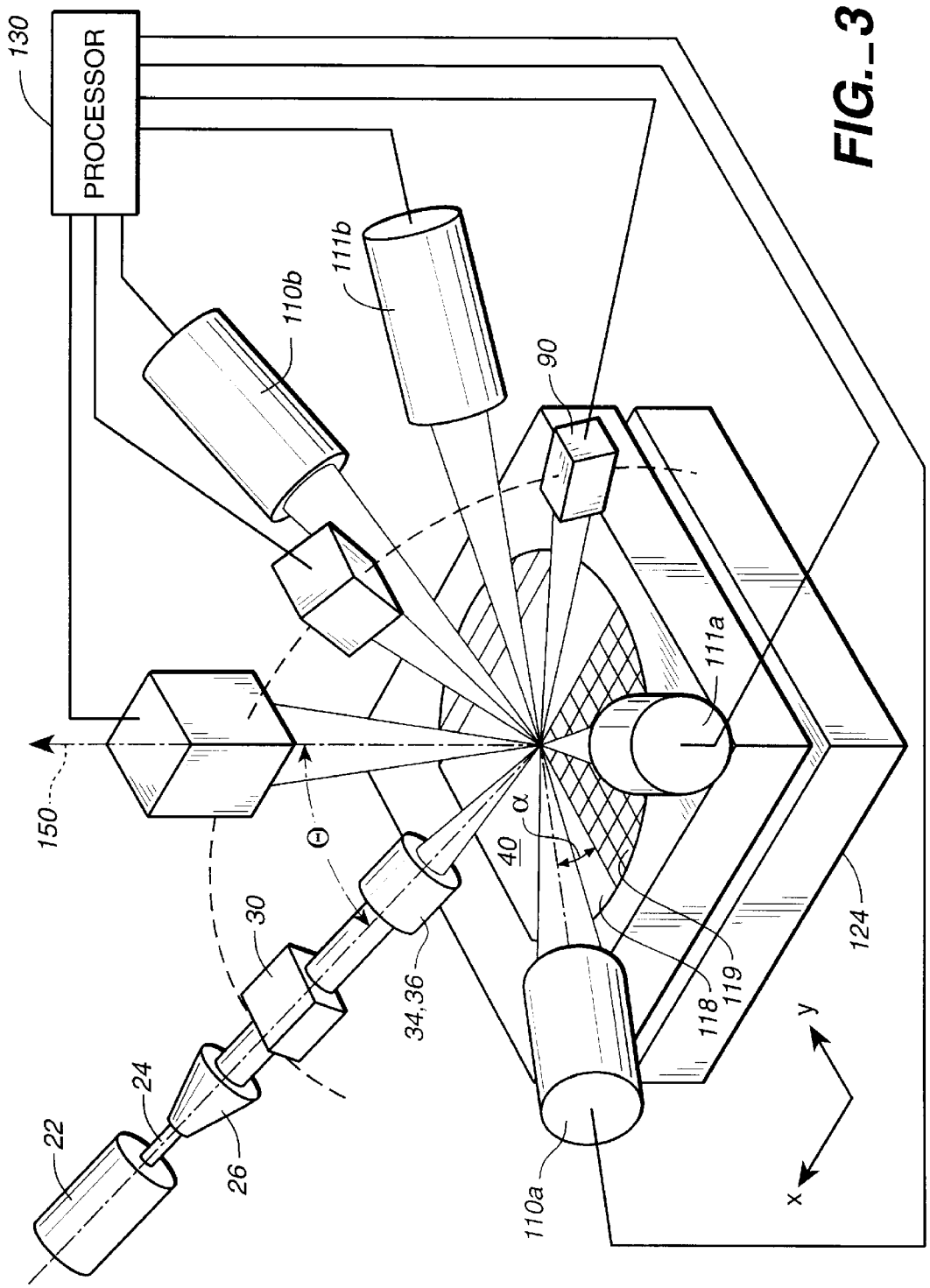
FIG._3

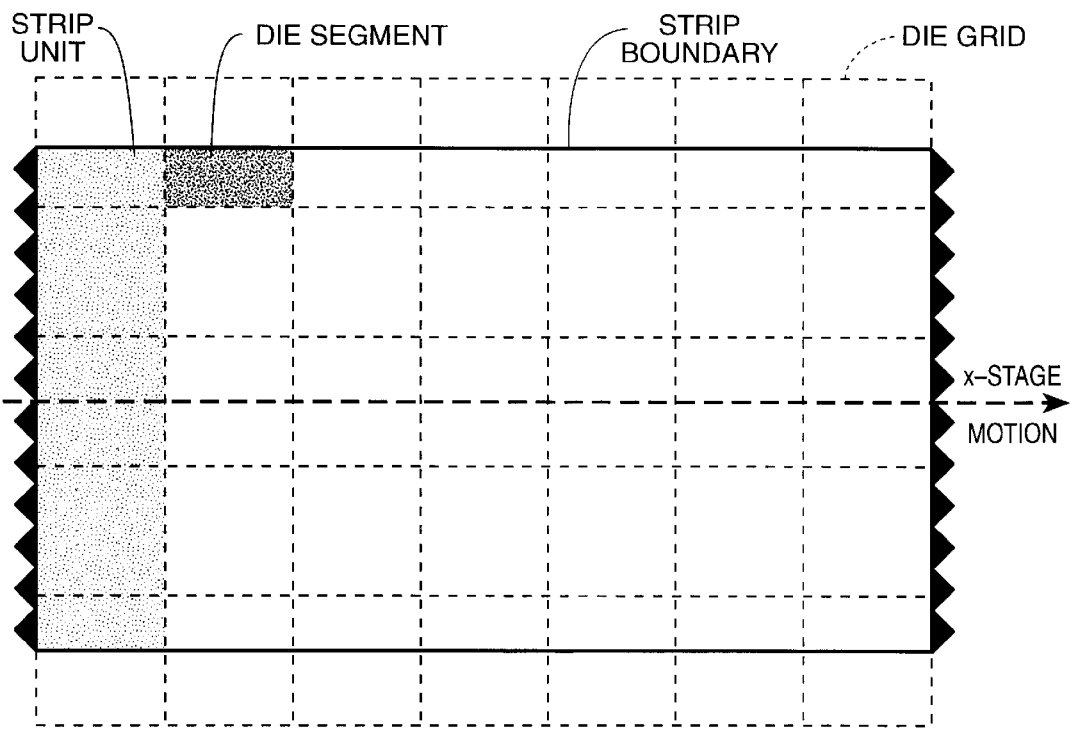
FIG._5
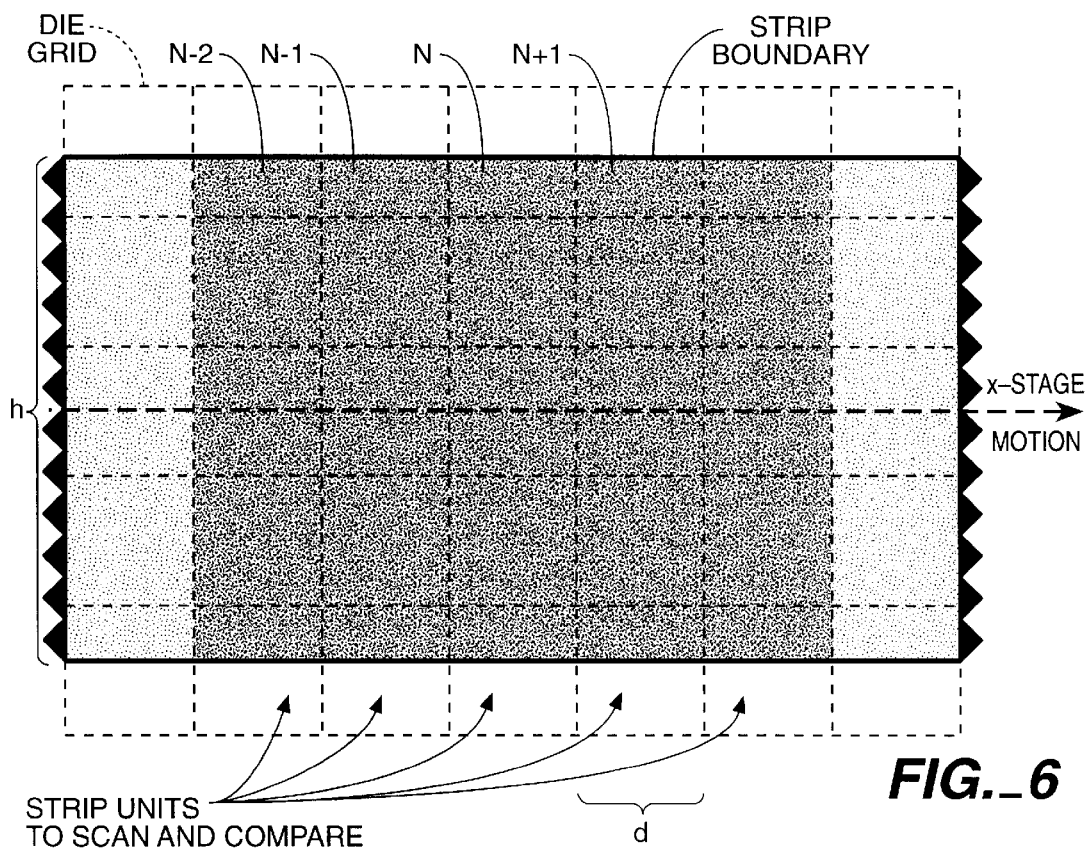
FIG._6

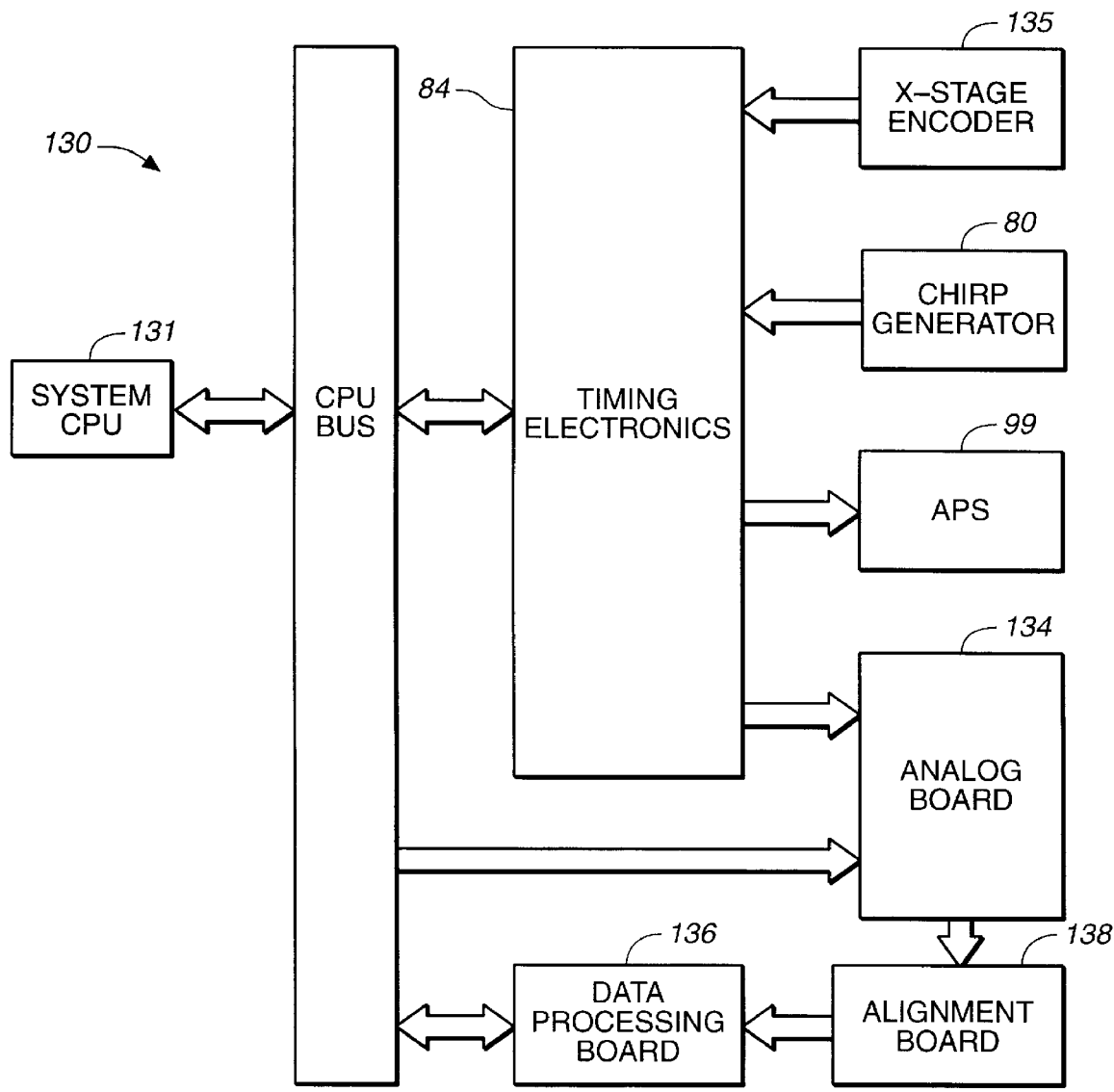
FIG._7

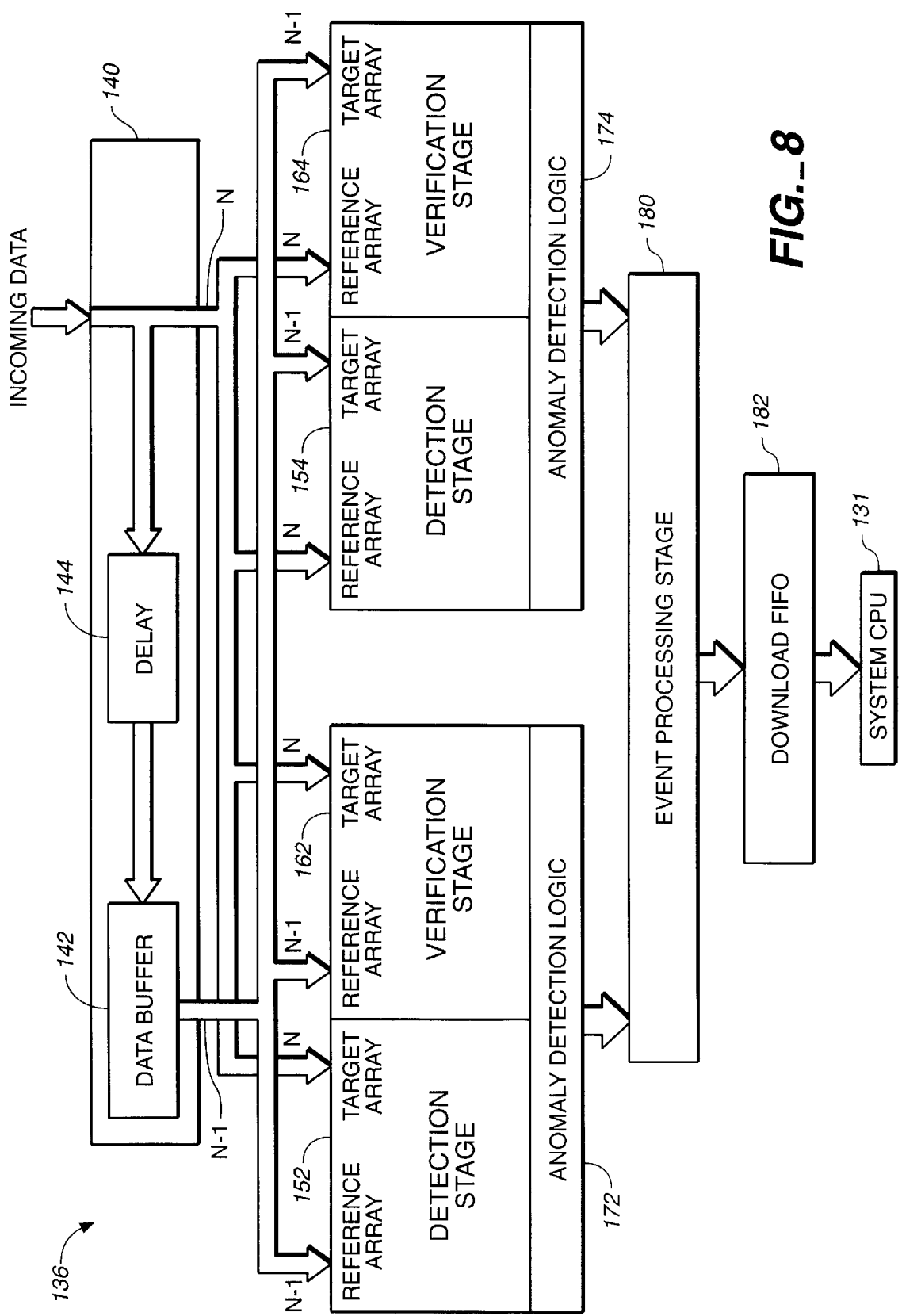
FIG._8

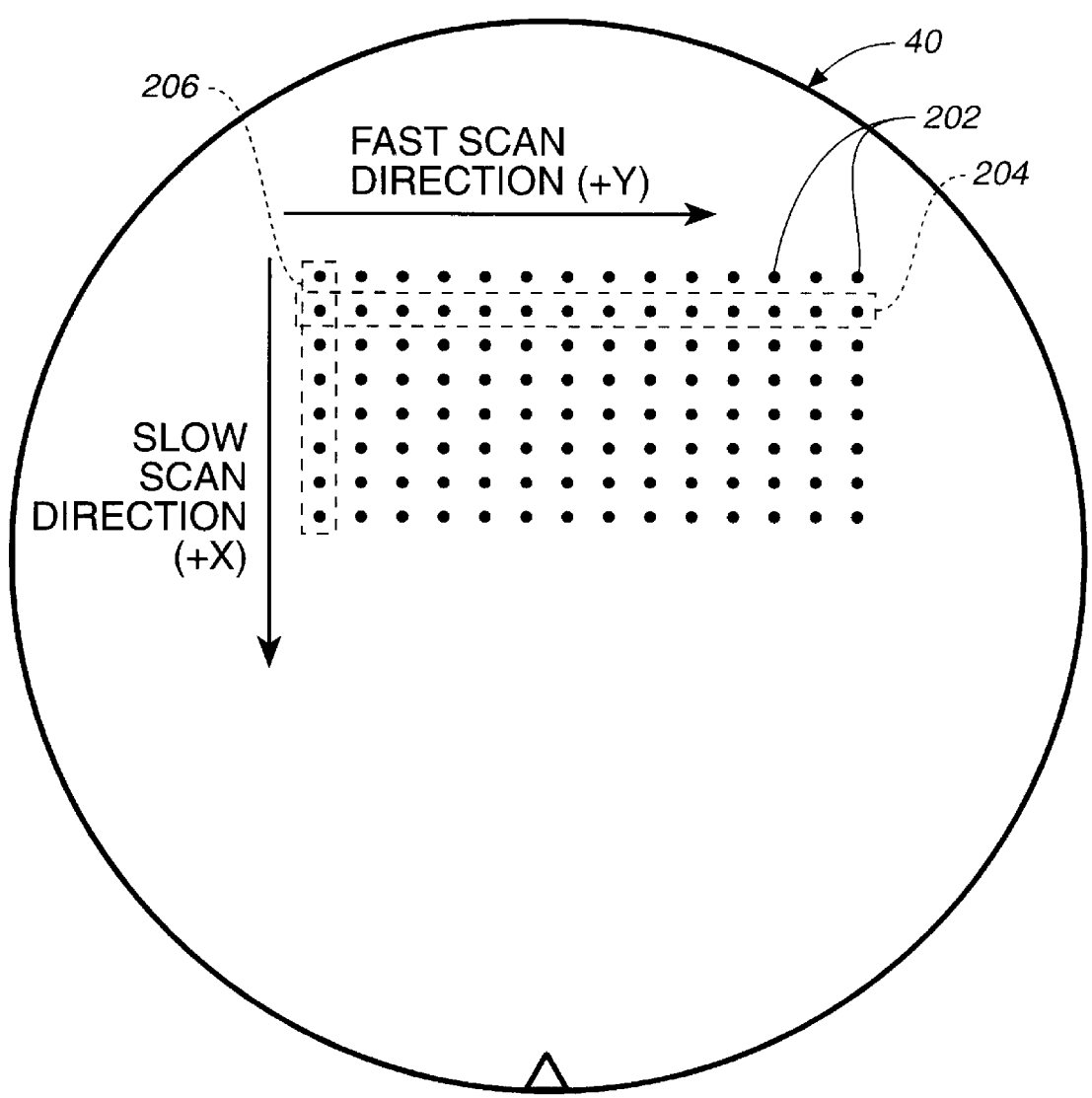
FIG._9

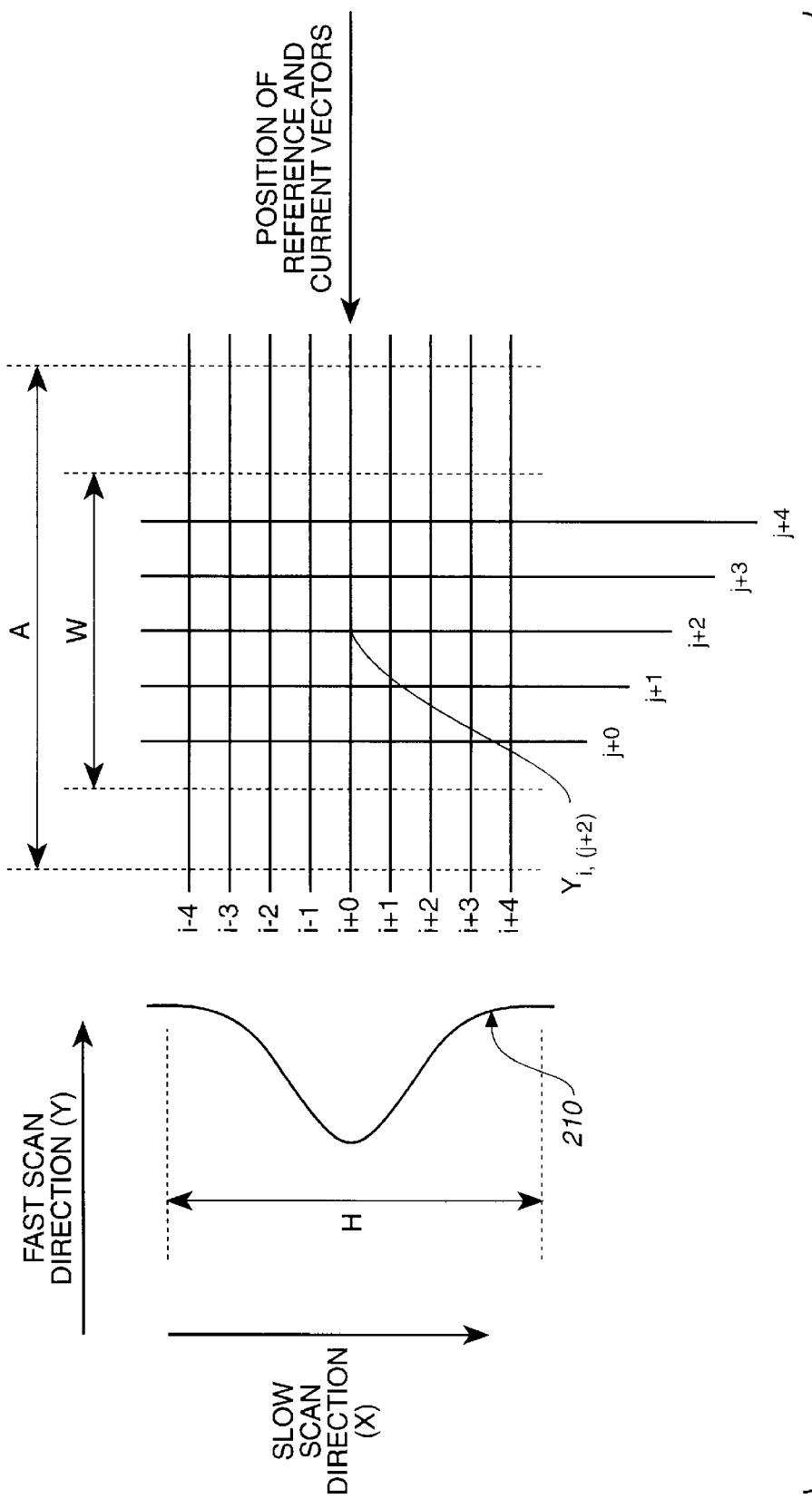
FIG._10A

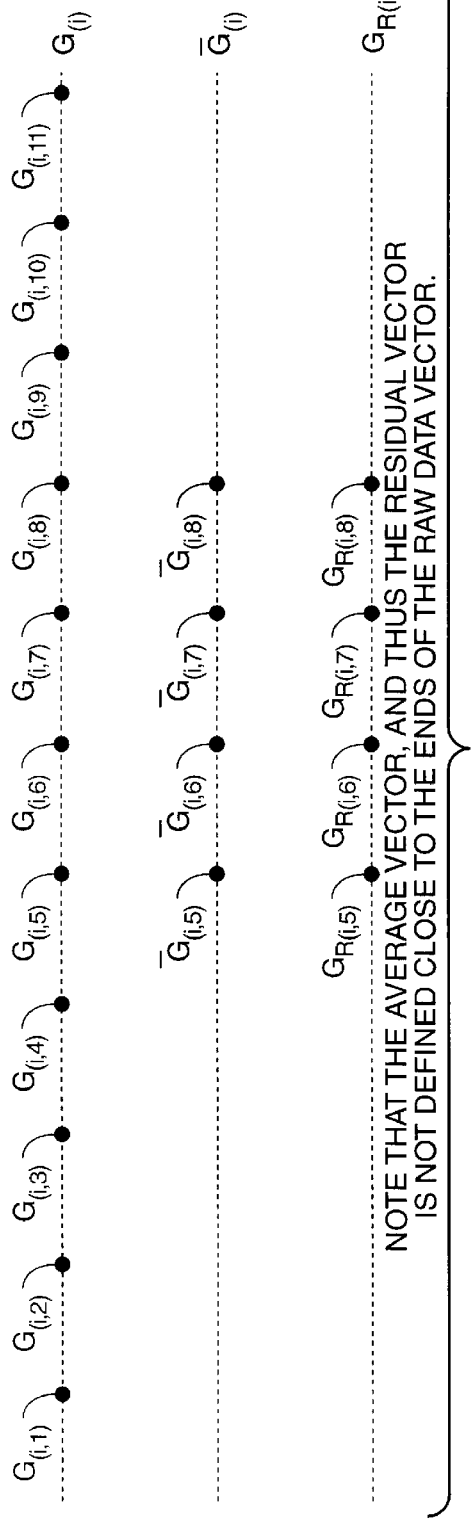
FIG._10B
NOTE THAT THE AVERAGE VECTOR, AND THUS THE RESIDUAL VECTOR IS NOT DEFINED CLOSE TO THE ENDS OF THE RAW DATA VECTOR.
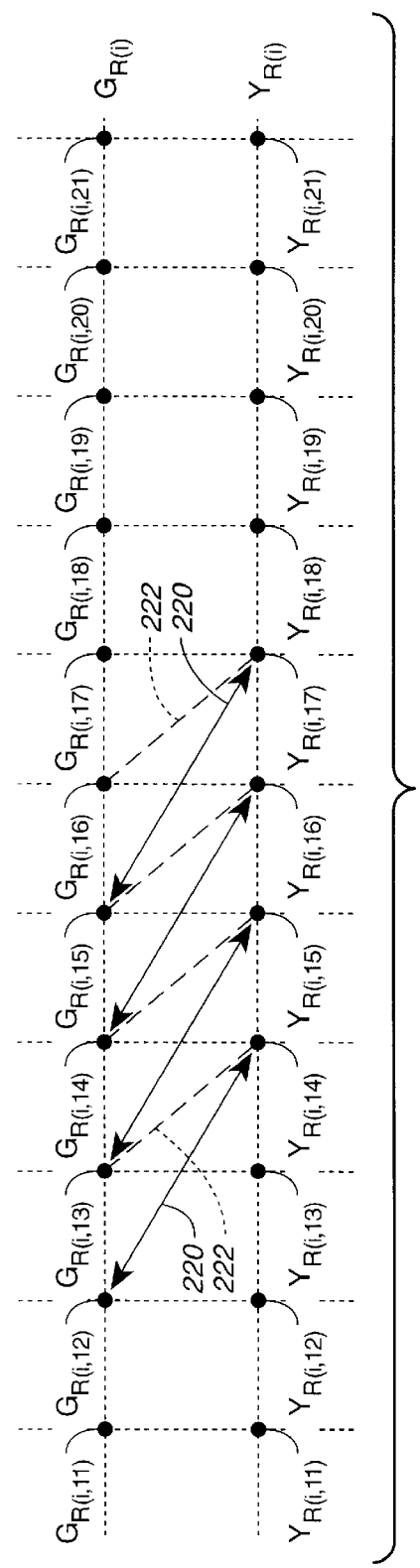
FIG._10C

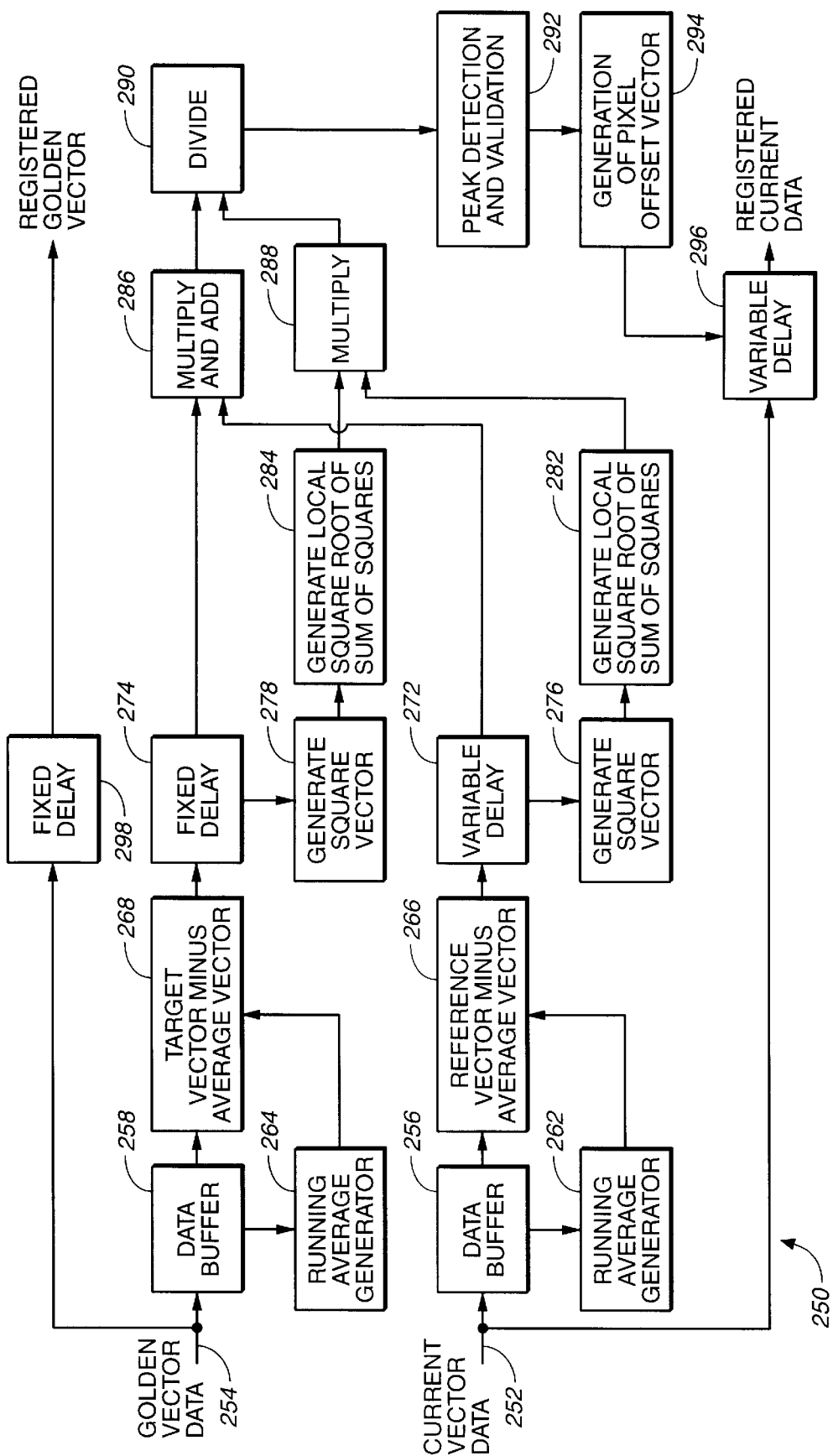
FIG._11

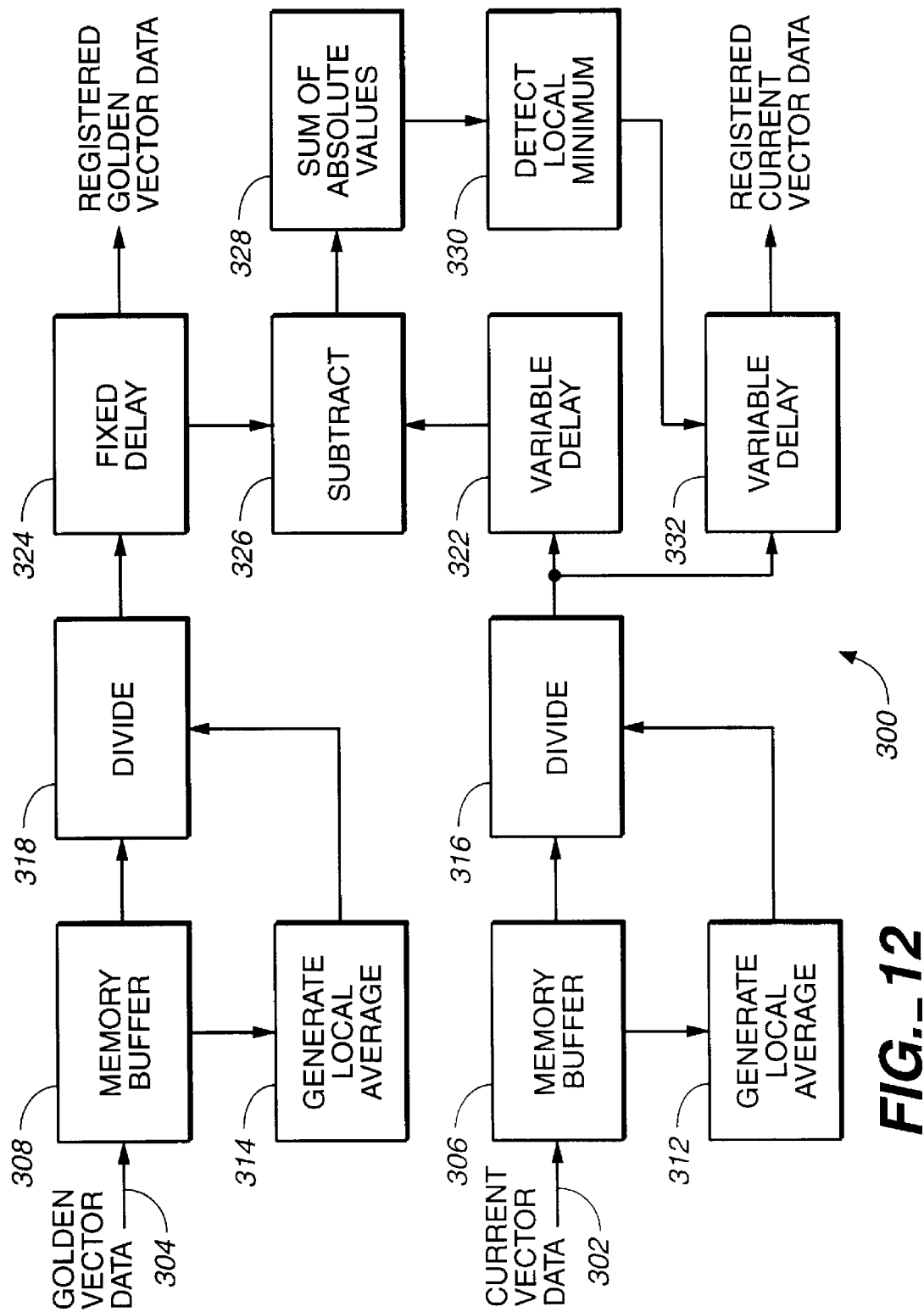
FIG._12

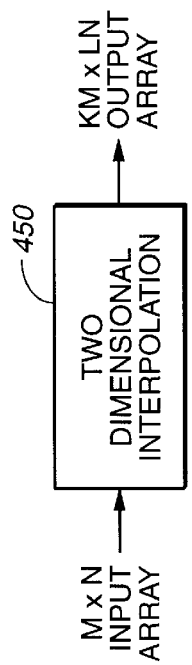
FIG._18
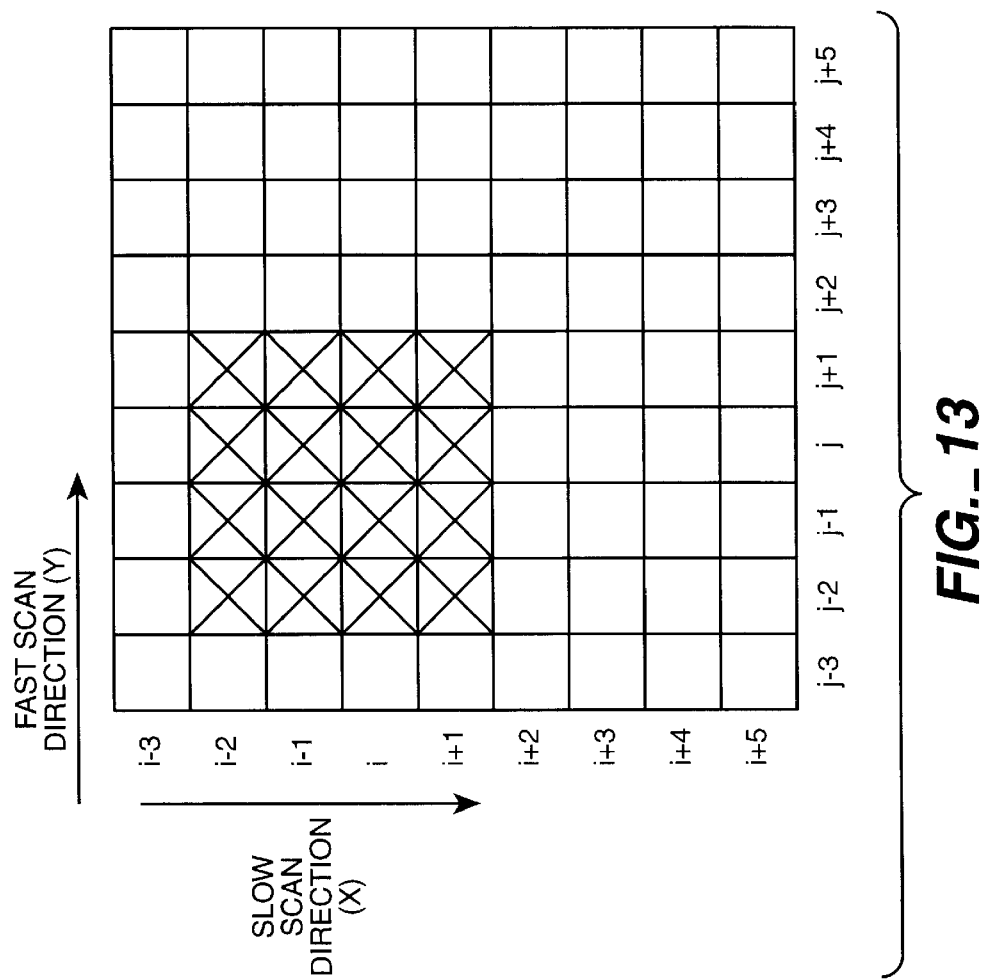
FIG._13

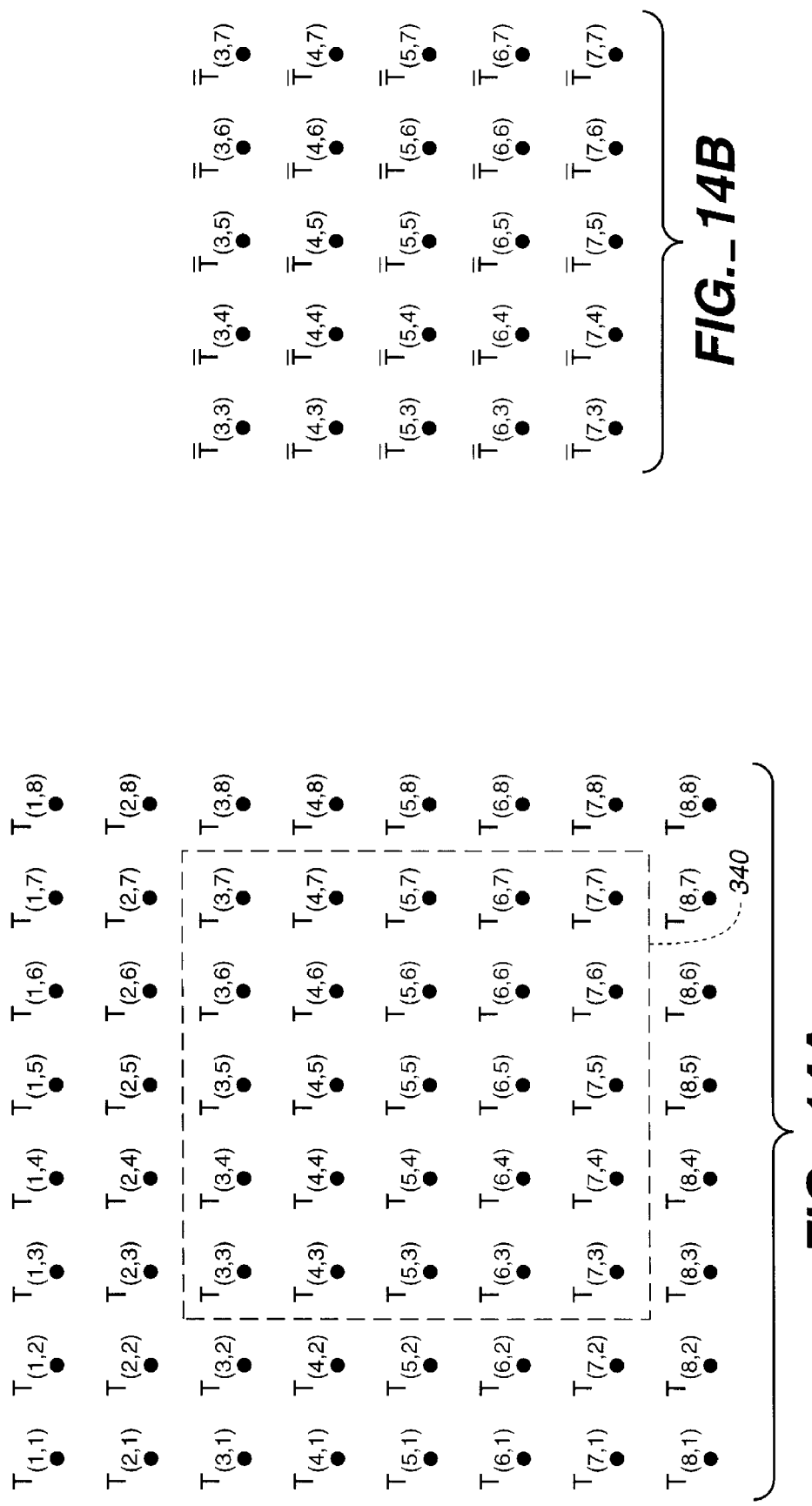
FIG._14B
FIG._14A

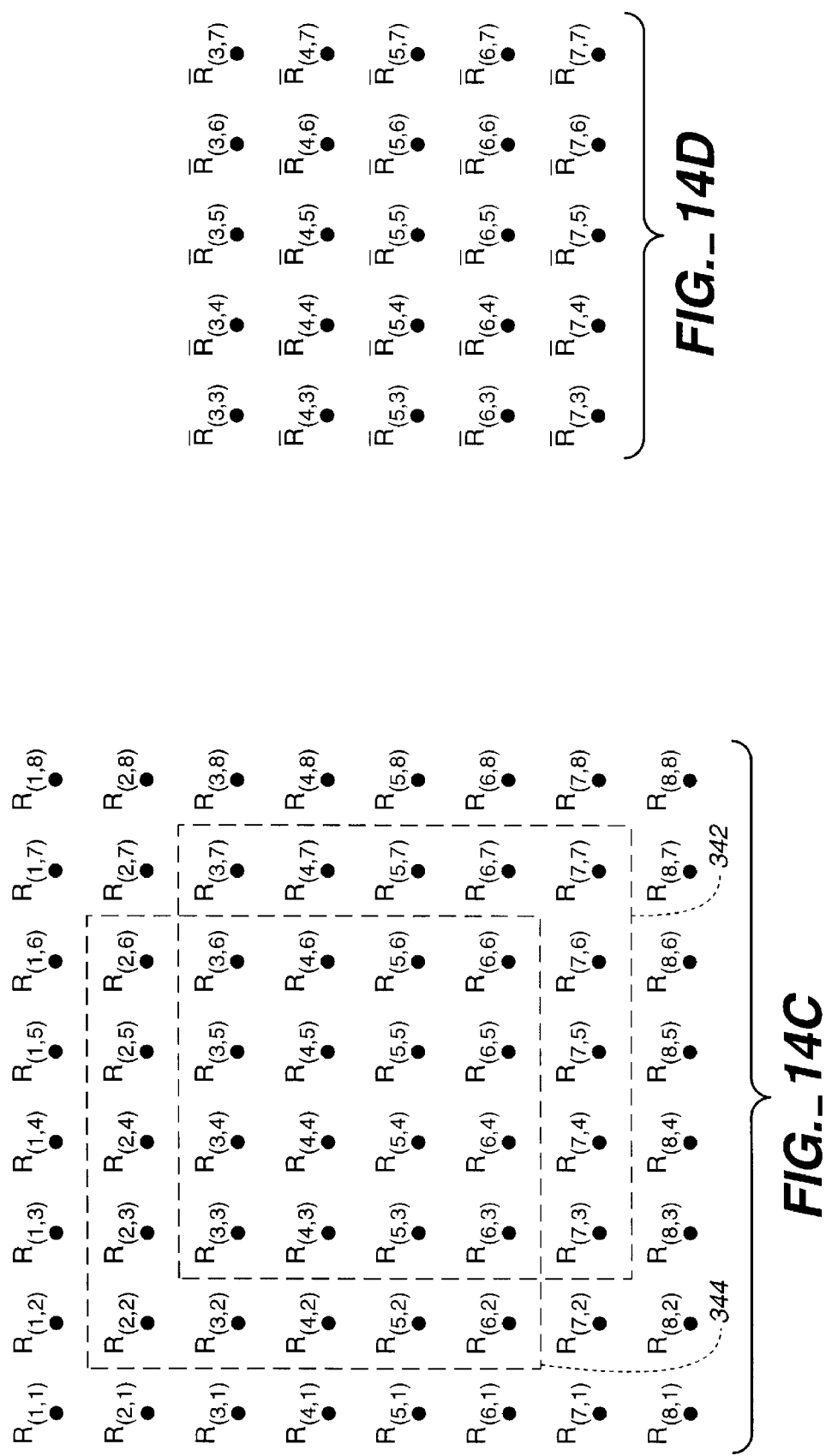

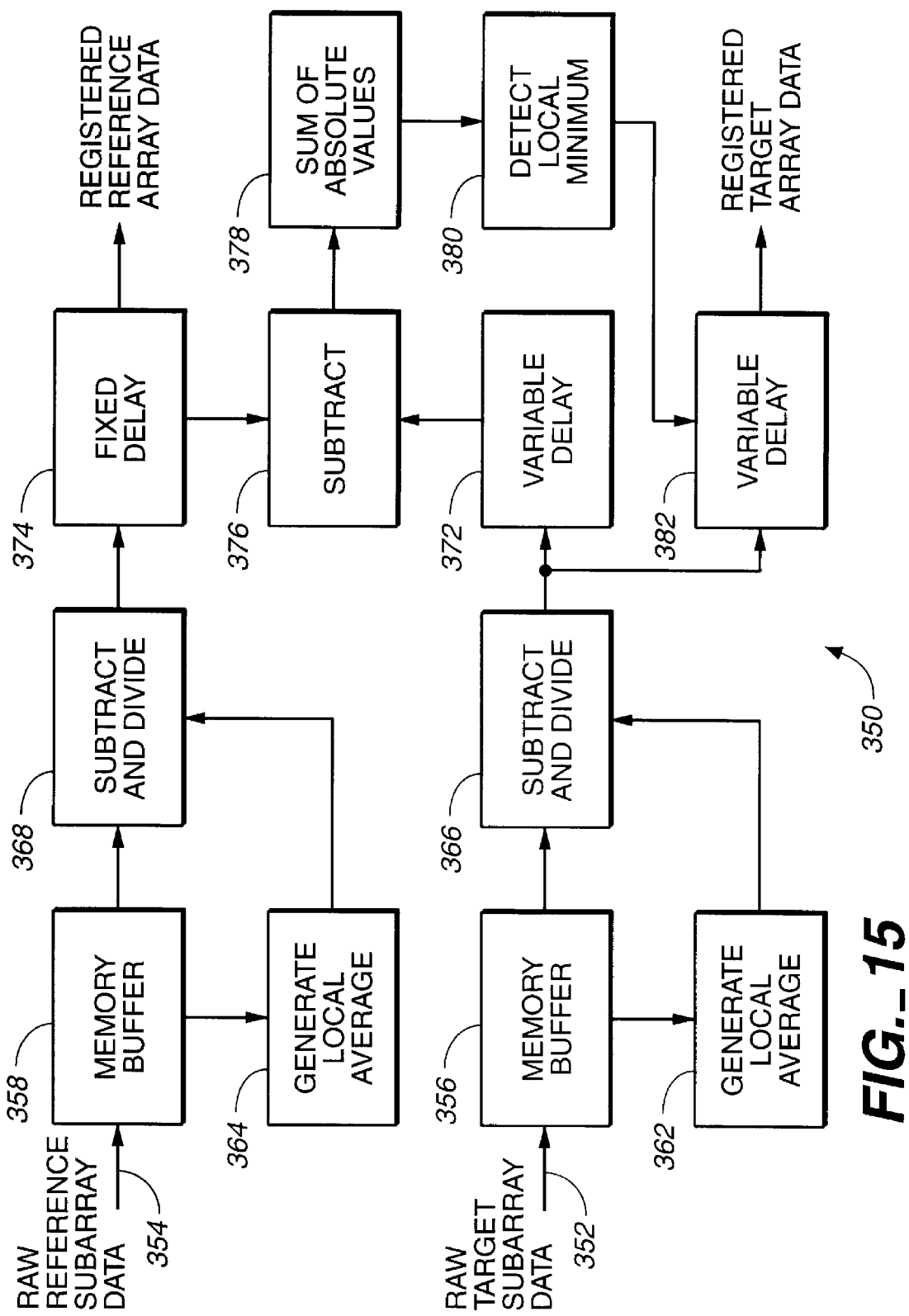
FIG._15

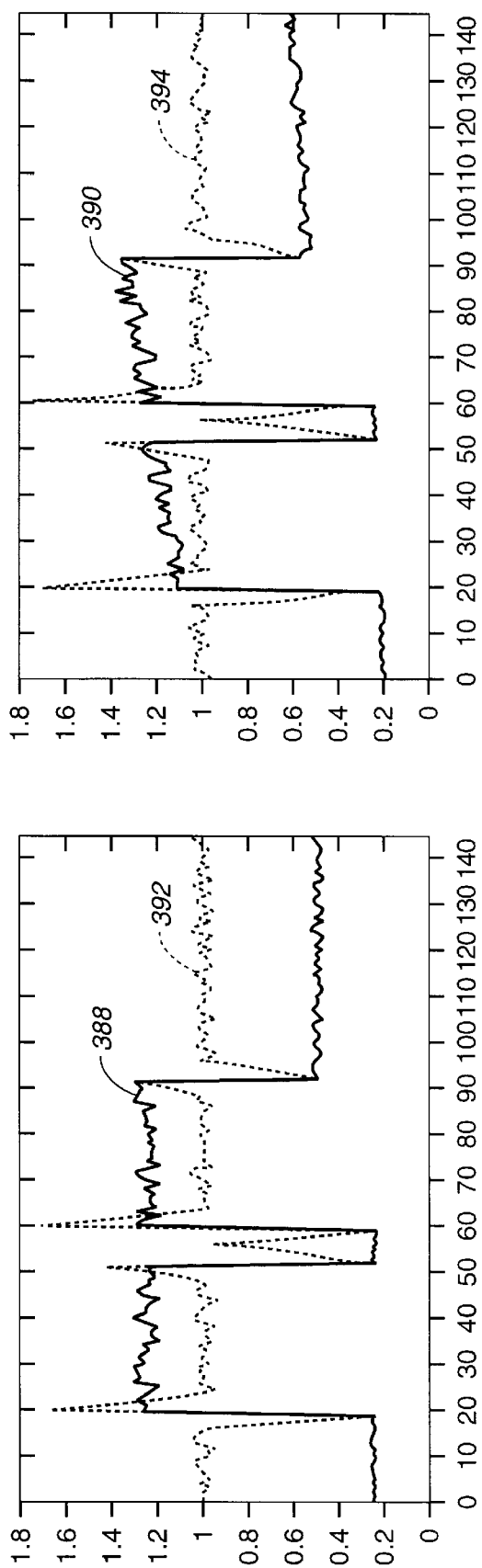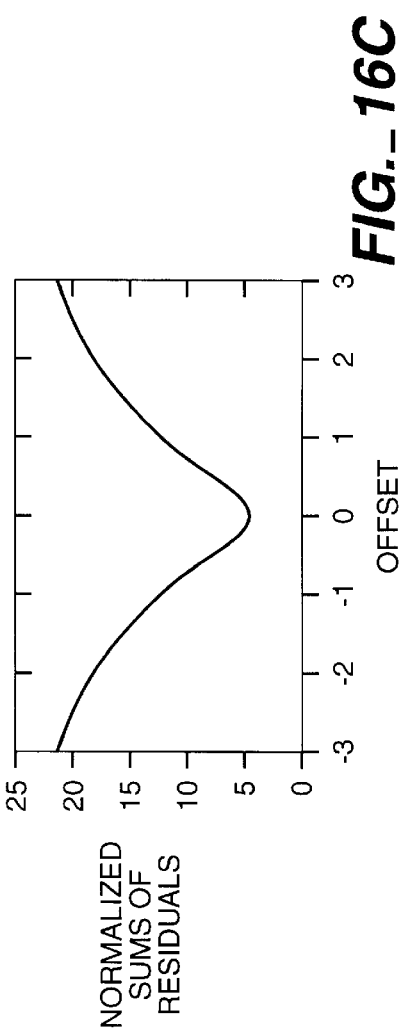

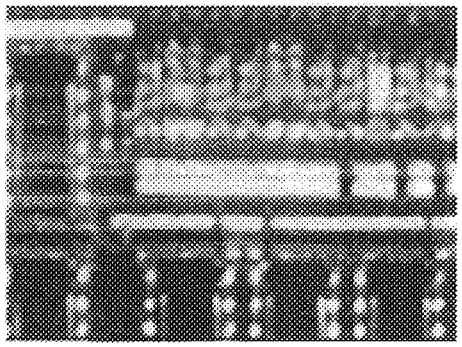
FIG._16D
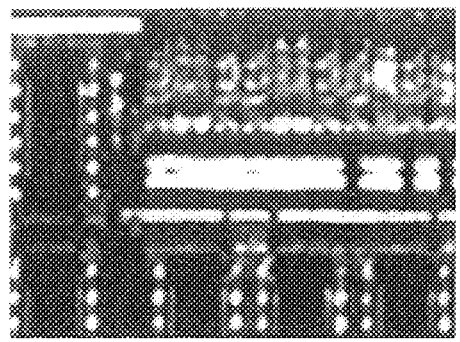
FIG._16E
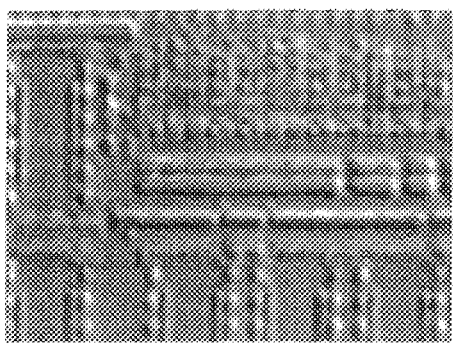
FIG._16F
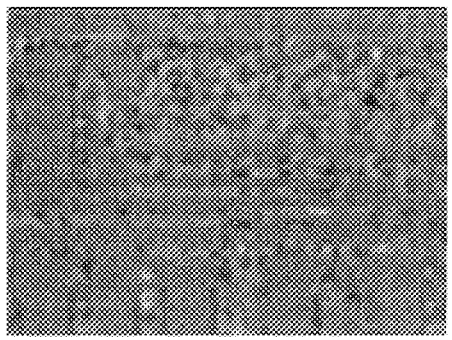
FIG._16G

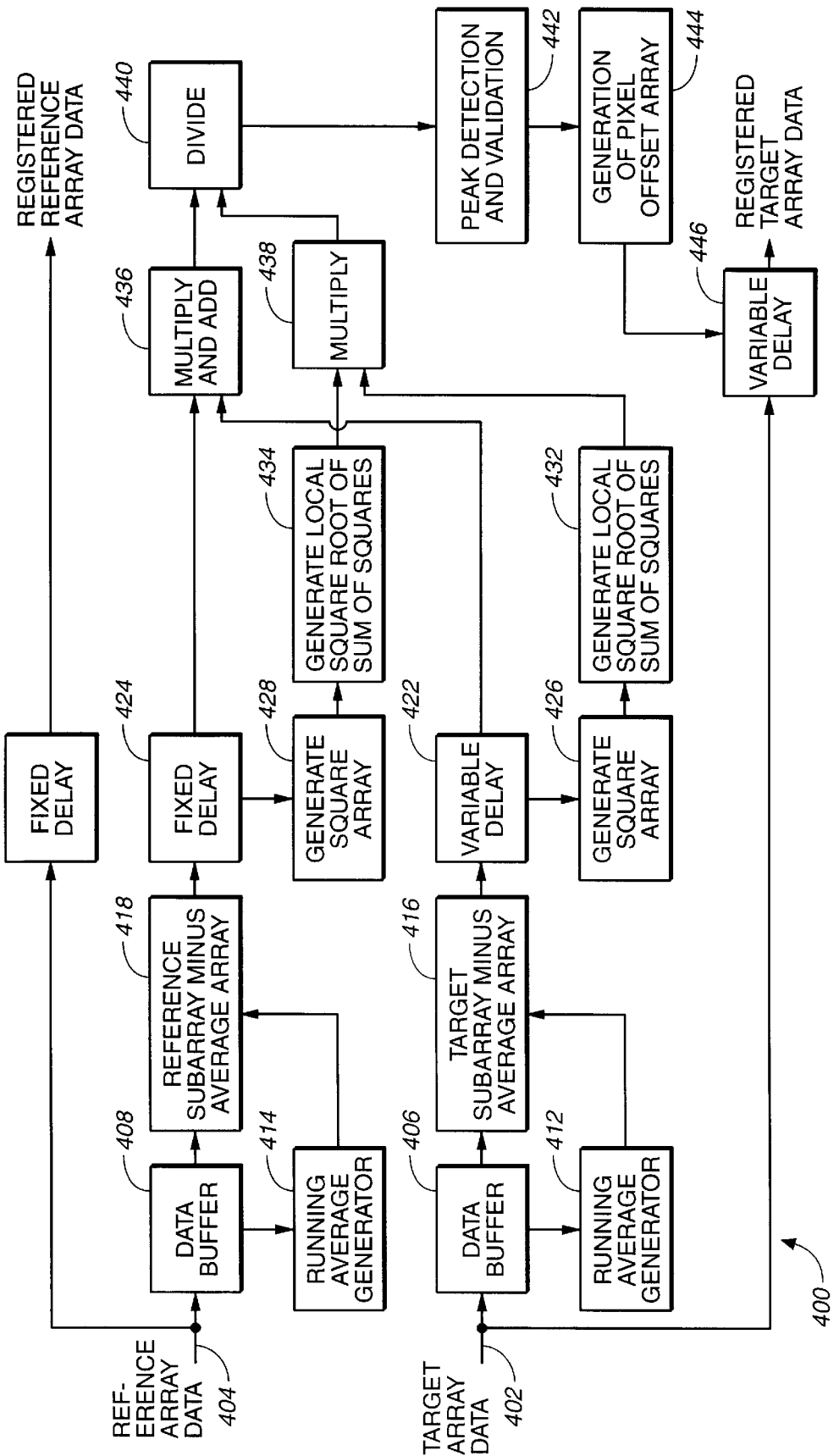
FIG._17

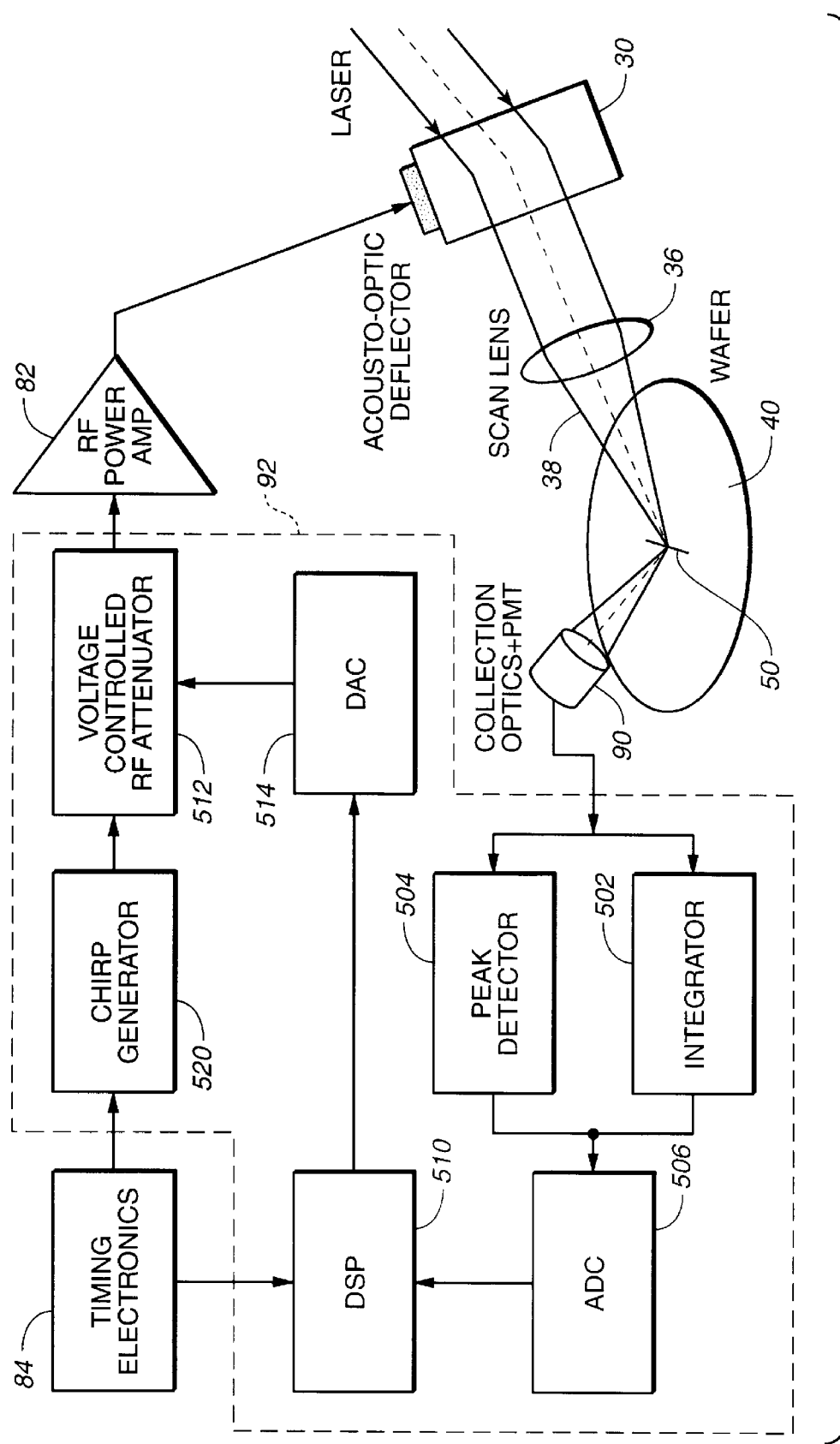
FIG._19

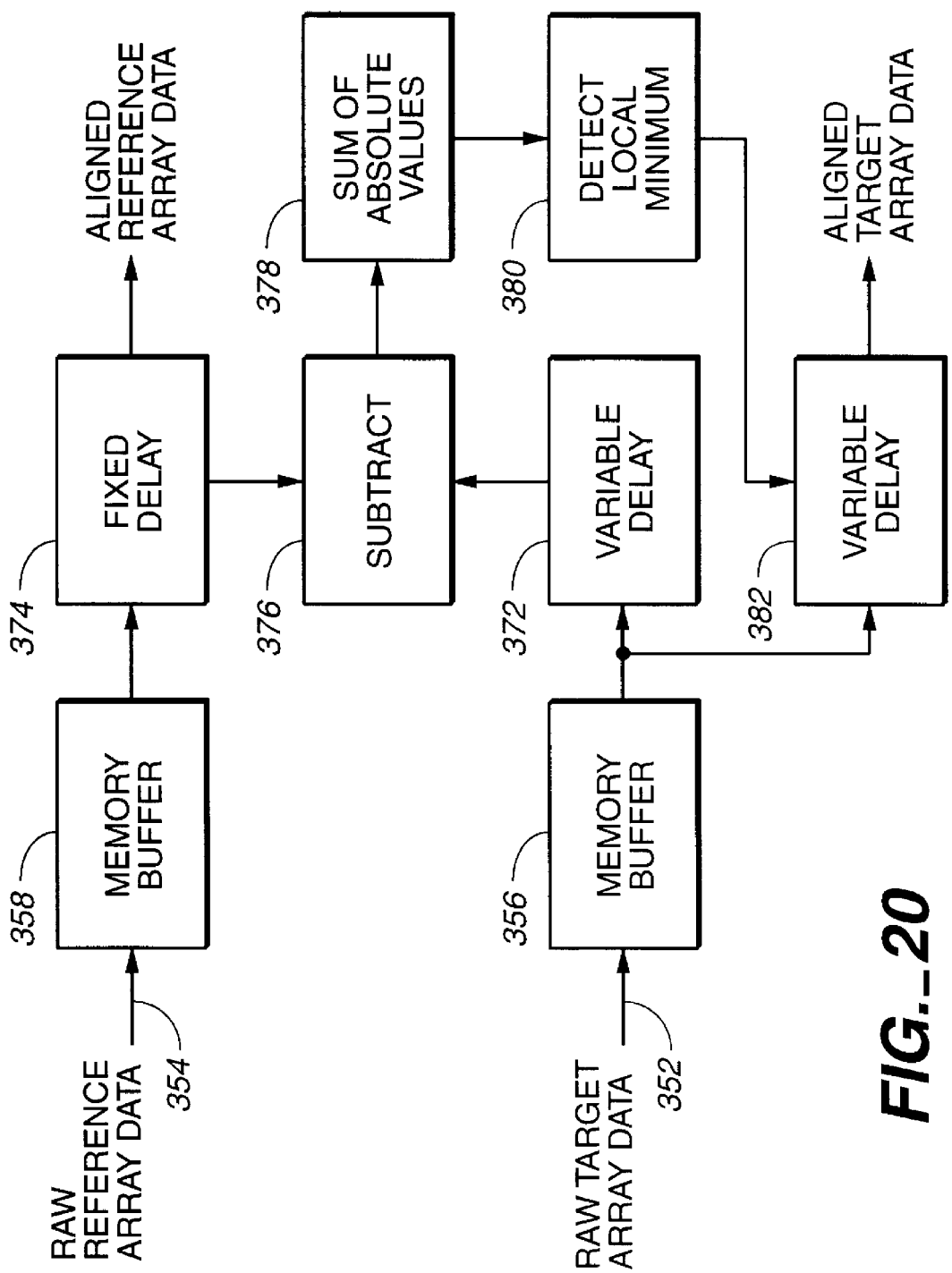
FIG._20

SURFACE INSPECTION SYSTEM WITH MISREGISTRATION ERROR CORRECTION AND ADAPTIVE ILLUMINATION

CROSS-REFERENCE TO RELATED APPLICATION

This application is a continuation-in-part application of U.S. patent application Ser. No. 08/536,862 filed Sep. 29, 1995, hereinafter referred to as the parent application.

BACKGROUND OF THE INVENTION

This invention relates in general to surface inspection systems and in particular to an improved surface inspection system employing misregistration error correction and adaptive illumination.

The improved surface inspection system of this application is particularly useful for inspecting anomalies of semiconductor wafers, photomasks, reticles, ceramic tiles and other surfaces. The size of semiconductor devices fabricated on silicon wafers has been continually reduced. The shrinking of semiconductor devices to smaller and smaller sizes has imposed a much more stringent requirement on the sensitivity of wafer inspection instruments which are called upon to detect contaminant particles and pattern defects that are small compared to the size of the semiconductor devices. At the same time, it is desirable for wafer inspection systems to provide an adequate throughput so that these systems can be used for in-line inspection to detect wafer defects. One example is the SURFSCAN® AIT system marketed by Tencor Instruments of Milpitas, Calif.

An anomaly detection system typically detects light scattered, reflected or otherwise modified by small areas of a sample. The data associated with such small areas are processed for anomaly detection. If the data for a small area is erroneously associated with a different small area, this may cause errors in identifying anomalies; such errors are known as misregistration errors.

In a laser scanning system such as the SURFSCAN® AIT, an acousto-optic deflector (AOD) may be used to sweep the laser beam across the surface to be inspected. In a system of this type, misregistration errors can arise for a number of reasons. Thus, jitter in firing the start of the sweep signal of the AOD and non-linearity in the chirp rate of the AOD can cause misregistration errors. While the AOD is used to cause the laser beam to sweep in one direction, a mechanical stage is used to move the wafer surface in a direction transverse to the sweep direction of the laser beam. Thus, mechanical instability of the mechanical stage or other mechanical vibrations in the optical/mechanical system can also result in misregistration. Pointing instability of the laser used for providing the scanning beam can also cause misregistration. Misregistration errors can arise in the direction of sweep of the laser beam as well as in a direction transverse to the sweep direction. Where there are repeating patterns on or in the sample, sometimes it is advantageous to compare corresponding areas of the sample for anomaly detection. Misregistration errors will also cause such comparison to yield erroneous results. It is, therefore, desirable to provide an improved surface inspection system where misregistration errors due to the above described reasons and other reasons are corrected. In this context, correction of misregistration includes reducing as well as eliminating errors due to misregistration.

SUMMARY OF THE INVENTION

This invention is based on the observation that in many optical inspection systems, data samples in the same neighborhood are correlated so that such correlation may be used for reducing or correcting misregistration. In a laser scanning system, for example, the point spread function of the scanning laser beam is such that data samples on adjacent scan lines are highly correlated and can be taken advantage of in misregistration correction. One aspect of the invention is directed towards a method for correcting misregistration errors in a system for detecting anomalies in a specimen such as a semiconductor wafer, said system illuminating a surface of a specimen at a two-dimensional array of locations in rows and columns. The method comprises the steps of generating a two-dimensional array of data samples in rows and columns, each data sample representing light modified by the specimen at a corresponding location in the two-dimensional array of locations of the specimen, and defining one-dimensional groups of data samples, each group of data samples or portion thereof defining a vector. The method further comprises, for at least one vector, providing a reference vector that is an average of selected vectors of data samples; and processing the at least one vector and the reference vector to correct for misregistration.

Another aspect of the invention is directed towards a method for correcting misregistration errors in a system for detecting anomalies in a specimen such as a semiconductor wafer, said system illuminating a surface of the specimen at a two-dimensional array of locations in rows and columns. The method comprises the steps of generating a two-dimensional array of data samples in rows and columns, each data sample in a row and column representing light modified by the specimen at a corresponding location in the two-dimensional row and column of locations. The method further comprises comparing the data samples of a target subarray and the data samples of each of a plurality of reference subarrays, or between signals derived therefrom, the target and the reference subarrays having the same dimensions, one of the reference subarrays being at a reference position and the remaining reference subarrays being offset from the reference position by at least one row and/or column of data samples to select a pair of offset values; and repositioning the target subarray according to the pair of offset values.

Yet another aspect of the invention is directed towards a method for correcting misregistration errors in a system for detecting anomalies in a specimen such as a semiconductor wafer, said system illuminating a surface of the specimen at a two-dimensional array of locations in rows and columns. The method comprises the steps of generating a two-dimensional array of data samples in rows and columns, each data sample in a row and column representing light modified by the specimen at a corresponding location in the row and column of locations. The method further comprises crosscorrelating a target subarray and each of a plurality of reference subarrays of data samples, or signals derived therefrom, to obtain a plurality of sets of crosscorrelation values, the target and the reference subarrays having the same dimensions, one of the reference subarrays being at a reference position and the remaining reference subarrays being offset from the reference position by at least one row and/or column of data samples; and selecting the reference subarray that corresponds to a set of crosscorrelation values according to a criterion.

One more aspect of the invention is directed towards a method for detecting anomalies in the specimen such as a semiconductor wafer, said method comprising the steps of scanning a light beam across the specimen along scan lines and detecting light originating from the light beam after such light has been modified by the specimen. The method further comprises controlling intensity of the light beam as a function of reference data to correct for variations in the detected light caused by optical characteristics of the specimen apart from the anomalies.

Yet another aspect of the invention is directed towards an apparatus for detecting anomalies in a specimen such as a semiconductor wafer, comprising means for scanning a light beam across the specimen along scan lines and a detector device detecting light originating from the light beam after such light has been modified by the specimen; and means for controlling intensity of the light beam as a function of reference data to correct for variations in the detected light caused by optical characteristics of the specimen apart from the anomalies.

Yet one more aspect of the invention is directed towards an apparatus for correcting misregistration errors in a system for detecting anomalies in a specimen such as a semiconductor wafer, said system illuminating a surface of the specimen at a two-dimensional array of locations in rows and columns. The apparatus comprises means for generating a two-dimensional array of data samples in rows and columns, each data sample representing light modified by the specimen at a corresponding location in the two-dimensional array of locations, and means for defining one-dimensional groups of data samples, each group of data samples or a portion thereof defining a vector. The apparatus further comprises means for providing a reference vector that is an average of selected vectors of data samples for at least one vector in the two-dimensional array; and means for processing the at least one vector and the reference vector to correct for misregistration.

An additional aspect of the invention is directed towards an apparatus for correcting misregistration errors in a system for detecting anomalies in a specimen such as a semiconductor wafer, said system illuminating a surface of the specimen at a two-dimensional array of locations in rows and columns. The apparatus comprises means for generating a two-dimensional array of data samples in rows and columns, each data sample in a row and column representing light modified by the specimen at a corresponding location in the two-dimensional array of locations. The apparatus further comprises means for comparing the data samples of a target subarray and the data samples of each of a plurality of reference subarrays, or between signals derived therefrom, the target and the reference subarrays having the same dimensions, one of the reference subarrays being at a reference position and the remaining reference subarrays being offset from the reference position by at least one row and/or column of data samples to select a pair of offset values; and means for repositioning the target subarray according to the pair of offset values.

Another aspect of the invention is directed towards an apparatus for correcting misregistration errors in the system for detecting anomalies in a specimen such as a semiconductor wafer, said system illuminating a surface of the specimen at a two-dimensional array of locations in rows and columns. The apparatus comprises means for generating a two-dimensional array of data samples in rows and columns, each data sample in a row and column representing light modified by the specimen at a corresponding location in the two-dimensional array of locations. The apparatus further includes means for crosscorrelating a target subarray and each of a plurality of reference subarrays of data samples, or signals derived therefrom, to obtain a plurality of sets of crosscorrelation values, the target and the reference subarrays having the same dimensions, one of the reference subarrays being at a reference position and the remaining reference subarrays being offset from the reference position by at least one row and/or column of data samples; and means for selecting the reference subarray that corresponds to a set of crosscorrelation values according to a criterion.

BRIEF DESCRIPTION OF THE DRAWINGS

FIG. 1A is a schematic view of an elliptical-shaped illuminated area or spot on a surface to be inspected to illustrate the invention.

FIG. 1B is a graphical illustration of the illumination intensity across the width or short axis of the elliptical spot of FIG. 1A for defining a boundary of the spot and to illustrate the invention and illustrating a point spread function of the illumination beam.

FIG. 1C is a schematic view of three positions of an illuminated area on a surface to be inspected to illustrate the scanning and data gathering process of the system of this invention.

FIG. 2 shows partially in perspective and partially in block diagram form a system for inspecting anomalies of a semiconductor wafer surface to illustrate the preferred embodiment of the invention.

FIG. 3 is a perspective view showing in more detail the illumination and collection features of the system of FIG. 2.

FIG. 4 is a schematic diagram of sweep and "mechanical" scan axes to illustrate the data acquisition process of the invention.

FIG. 5 is a schematic view of a portion of a patterned wafer surface illustrating the intersection of a strip unit with a die grid to illustrate the data processing subsystem of this invention.

FIG. 6 is a schematic view illustrating a portion of a patterned wafer surface illustrating a number of strip units and the anomaly detection and verification processes of FIGS. 7 and 8.

FIG. 7 is a system electronics functional block diagram of the present system of the invention.

FIG. 8 is a functional block diagram of the data processing board portion of the system of FIG. 7 to illustrate the preferred embodiment of the invention.

FIG. 9 is a schematic top view of a semiconductor wafer having a two-dimensional array of locations relative to a fast scan direction and a direction of sweep of the AOD and a slow scan direction using a mechanical stage to illustrate the invention.

FIG. 10A is a schematic view of reference and current vectors in reference to a coordinate system in the alignment board of FIG. 7 to illustrate the preferred embodiment of the invention.

FIG. 10B is a schematic view of the reference vector of FIG. 10A, and of average and residual reference data samples to illustrate the invention.

FIG. 10C is a schematic view of reference and current vectors to illustrate a process of crosscorrelation or residual minimization.

FIG. 11 is a functional block diagram for image registration using normalized crosscorrelation of a current vector and a reference vector for correcting misalignment performed by the alignment board of FIG. 7 to illustrate one aspect of the invention.

FIG. 12 is a functional block diagram for correcting misregistration using normalized residual minimization in the alignment board of FIG. 7 to illustrate another aspect of the invention.

FIG. 13 is a schematic diagram to illustrate the generation of a local average in a normalization process of a current vector and a reference vector performed by the alignment board of FIG. 7 to illustrate one feature of the invention in FIG. 12.

FIG. 14A is a schematic view of a two-dimensional array of data samples in a target subarray taken from the two-dimensional array in one of the strip units, such as strip unit N of FIG. 6.

FIG. 14B is a schematic view of a two-dimensional array of average data samples obtained from the target array of FIG. 14A.

FIG. 14C is a schematic view of a two-dimensional subarray of data samples taken from a two-dimensional array of data samples in a reference strip unit, such as strip unit N−1 in FIG. 6.

FIG. 14D is a schematic view of a two-dimensional array of average data samples obtained from the reference array of FIG. 14C.

FIG. 15 is a functional block diagram for image registration using normalized residual minimization of a target subarray and a reference subarray for correcting misalignment performed by the alignment board of FIG. 7 to illustrate one aspect of the invention.

FIGS. 16A and 16B are graphical plots illustrating two normalized vectors to illustrate the effects of normalization in FIGS. 12, 13 and 15.

FIG. 16C is a graphical plot of the normalized sums of residuals versus offset to illustrate the processes in FIGS. 12 and 15.

FIGS. 16D–16G are computer plots of, respectively, a reference image, a target image, a residual image before alignment and a residual image after alignment using the alignment board of FIG. 7 to illustrate the invention.

FIG. 17 is a functional block diagram for image registration using normalized crosscorrelation of a target subarray and a reference subarray for correcting misalignment performed by the alignment board of FIG. 7 to illustrate one aspect of the invention.

FIG. 18 is a functional block diagram for interpolation of detected intensity values to obtain the array of data samples of FIG. 9.

FIG. 19 shows partially in perspective and partially in block diagram form the surface inspection system of FIGS. 2 and 3, where the illumination beam is modulated to compensate for variations of detected light intensity caused by the optical characteristics of the specimen apart from anomalies.

FIG. 20 is a functional block diagram for correcting image misregistration in the system of FIG. 19 using adaptive illumination and residual minimization.

For simplicity in description, identical components are labelled by the same numerals in this application.

DETAILED DESCRIPTION OF THE PREFERRED EMBODIMENTS

FIG. 1A is a schematic view of an elliptical-shaped illuminated area (or spot) of a surface inspected by the system of this invention to illustrate the invention. As explained below, the laser beam illuminating the surface inspected approaches the surface at a grazing angle, so that even though the illumination beam has a generally circular cross-section, the area illuminated is elliptical in shape such as area 10 in FIG. 1A. As known to those skilled in the art, in light beams such as laser beams, the intensity of the light typically does not have a flat distribution and does not fall off abruptly to zero across the boundary of the spot illuminated, such as at boundary 10a of spot 10 of FIG. 1A. Instead, the intensity falls off at the outer edge of the illuminated spot at a certain inclined slope, so that instead of sharp boundaries such as boundary 10a illustrated in FIG. 1A, the boundary is typically blurred and forms a band of decreasing intensity at increasing distance away from the center of the illuminated area.

In many lasers, the laser beam produced has a Gaussian intensity distribution, such as that shown in FIG. 1B. FIG. 1B is a graphical illustration of the spatial distribution of the illumination intensity in the Y direction of a laser beam that is used in the preferred embodiment to illuminate spot 10 of a surface to be inspected as shown in FIG. 1A, and thus is also the illumination intensity distribution across spot 10 in the Y direction. As shown in FIG. 1B, the illumination intensity has been normalized so that the peak intensity is 1, and the illumination intensity has a Gaussian distribution in the X direction as well as in the Y direction. Points 12 and 14 are at spatial locations y1 and y5 at which points the illumination intensity drops to $1/e^2$ of the peak intensity, where e is the natural number. The spot 10 is defined by the area within a boundary 10a where the illumination is $1/e^2$ of that of the maximum intensity of illumination at the center of the spot. The lateral extent of the spot 10 may then be defined to be the boundary 10a.

To maintain uniform detection sensitivity, the scanning light beam is preferably caused to scan short sweeps having a spatial span less than the dimension of the surface it is scanning, as illustrated in the preferred embodiment in FIG. 2, where these short sweeps are not connected together but are located so that they form arrays of sweeps.

The surface inspection system of this application will now be described with reference to FIGS. 2 and 3. As shown in FIG. 2, system 20 includes a laser 22 providing a laser beam 24. Beam 24 is expanded by beam expander 26 and the expanded beam 28 is deflected by acousto-optic deflector (AOD) 30 into a defected beam 32. The deflected beam 32 is passed through post-AOD and polarization selection optics 34 and the resulting beam is focused by telecentric scan lens 36 onto a spot 10 on surface 40 to be inspected, such as that of a semiconductor wafer, photomask or ceramic tile, patterned or unpatterned.

In order to move the illuminated area that is focused onto surface 40 for scanning the entire surface, the AOD 30 causes the deflected beam 32 to change in direction, thereby causing the illuminated spot 10 on surface 40 to be scanned along a sweep 50. As shown in FIG. 2, sweep 50 is preferably a straight line having a length which is smaller than the dimension of surface 40 along the same direction as the sweep. Even where sweep 50 is curved, its span is less than the dimension of surface 40 along the same general direction. After the illuminated spot has traversed along sweep 50, surface 40 of the wafer is moved by XY stage 124 (FIG. 3) parallel to the X axis in FIG. 2 so that the illuminated area of the surface moves along arrow 52 and AOD 30 causes the illuminated spot to scan a sweep 53 parallel to sweep 50 and in an adjacent position spaced apart from sweep 50 along the X axis to scan an adjacent sweep at a different X position. As described below, this small distance is preferably equal to about one quarter of the dimension of spot 10 in the X direction. This process is repeated until the illuminated spot has covered strip 54; at this point in time the illuminated area is at or close to the edge 54a. At such point, the surface 40 is moved by XY stage 124 along the Y direction by about the length of sweep 50 in order to scan and cover an adjacent strip 56, beginning at a position at or close to edge 56a. The surface in strip 56 is then covered by short sweeps such as 50 in a similar manner until the other end or edge 56b of strip 56 is reached at which point surface 40 is again moved along the X direction for scanning strip 58. This process is repeated prior to the scanning of strip 54, 56, 58 and continues after the scanning of such strips until the entire surface 40 is scanned. Surface 40 is therefore scanned by scanning a plurality of arrays of sweeps the totality of which substantially covers the entire surface 40.

The deflection of beam 32 by AOD 30 is controlled by chirp generator 80 which generates a chirp signal.

The chirp signal is amplified by amplifier 82 and applied to the transducer portion of AOD 30 for generating sound waves to cause deflection of beam 32 in a manner known to those skilled in the art. For a detailed description of the operation of the AOD, see "Acoustooptic Scanners and Modulators," by Milton Gottlieb in Optical Scanning, ed. by Gerald F. Marshall, Dekker 1991, pp. 615–685. Briefly, the sound waves generated by the transducer portion of AOD 30 modulate the optical refractive index of an acoustooptic crystal in a periodic fashion thereby leading to deflection of beam 32. Chirp generator 80 generates appropriate signals so that after being focused by lens 36, the deflection of beam 32 causes the focused beam to scan along a sweep such as sweep 50 in the manner described.

Chirp generator 80 is controlled by timing electronics circuit 84 which in the preferred embodiment includes a microprocessor. The microprocessor supplies the beginning and end frequencies f1, f2 to the chirp generator 80 for generating appropriate chirp signals to cause the deflection of beam 32 within a predetermined range of deflection angles determined by the frequencies f1, f2. The illumination sensor optics 90 and adaptive illumination control 92 are used to detect and control the level of illumination of spot 10. The optics 90 and adaptive illumination control 92 are explained in detail below in reference to FIGS. 19, 20.

Detectors such as detectors 110a, 110b, 111a, 111b of FIGS. 2 and 3 collect light scattered by anomalies as well as the surface and other structures thereon along sweeps such as sweep 50 and provide output signals to a processor 130 in order to detect anomalies and analyze their characteristics.

FIG. 3 is a perspective view of system 20 of FIG. 2 showing in more detail the arrangement of the collection/detection channels to illustrate the preferred embodiment. Surface 40 may be smooth (118) or patterned (119). The angle between the incident focused beam 38 and the normal direction 150 to the surface 40 is preferably in the range of about 10°–85° and more preferably within the range of 50°–80°; in FIG. 3, this angle is labelled θ. The four channels of collection are preferably at elevation angles α that will collect scattered light from 3°–30° from the plane of surface 40.

FIG. 1C is a schematic view of three positions of the illuminated area on a surface to be inspected to illustrate the scanning and data gathering process of system 20. As shown in FIG. 1C, at one instant in time, beam 38 illuminates an area 10 on surface 40. Spot 10 is divided into sixteen areas by grid lines x1–x5, y1–y5, where such areas are referred to below as resolution elements. In this context, the term "resolution element" is defined by reference to the taking of data samples across the intensity distributions along the X and Y axes, such as that in FIG. 1C, and by reference to subsequent data processing. The resolution element that is bounded by grid lines x2, x3 and y2, y3 is resolution element P shown as a shaded area in FIG. 1C. If there is an anomaly in this resolution element P, and if the light illuminating resolution element P has the intensity distribution as shown in FIG. 1B with a high intensity level between grid lines y2 and y3, light scattered by the anomaly will also have a high intensity. However, as the beam moves along the Y axis so that the area 10' is illuminated instead, resolution element P will still be illuminated but at the lower intensity level of that between grid lines y1 and y2; in reference to FIG. 1B, the intensity of the illumination is that between grid lines y1 and y2 in FIG. 1B. Therefore, if the sampling rate employed by the data processor 130 in FIG. 3 for processing light detected by the collection or collector channels 110a, 110b, 111a, 111b is such that a data sample is taken when the illuminating beam is in position 10 and when the illuminating beam is in position 10', then two data samples will be recorded. Thus for any resolution element such as P, a number of data points will be taken, one when the illumination is at a higher level as illustrated by data point D2 in FIG. 1B and another one when the illumination is at a lower level, illustrated at data point D1 in FIG. 1B. If position 10 is not the starting position of the sweep 50 illustrated in FIGS. 3 and 4, then two prior samples would have been taken prior to the time when the illuminating beam illuminates the surface 40 in position 10, so that the processor would have obtained two more data samples at points D3, D4 corresponding to the prior positions of the illuminating beam when light of intensity values between grid lines y3, y4 and between y4, y5 respectively illuminates such resolution element P (grid lines y1 through y5 would, of course, move with the location of the spot). In other words, four separate data samples at points D1–D4 would have been taken of the light scattered by an anomaly present in resolution element P as the illumination beam illuminates resolution element P when scanning along the Y direction.

In most laser beams, the beam intensity has a Gaussian intensity distribution not only in the Y direction but also in the X direction. For this reason, after the illuminating beam completes the scanning operation for scanning a sweep such as sweep 50 as shown in FIG. 2, and when the illuminating beam returns to position 74 for scanning the adjacent sweep 53 as shown in FIG. 2, it is desirable for the illuminated area along sweep 53 to overlap that of sweep 50 so that multiple samples or data points can again be taken also along the −X direction as well as along the Y direction.

Therefore, when the illumination beam is scanning along sweep 53 from starting position 74 as shown in FIG. 2, the area illuminated would overlap spot 10; this overlapping spot is 10" as shown in FIG. 1C, where the spot 10" is displaced along the −X direction relative to spot 10 by one quarter of the long axis of the ellipse 10 and 10".

Point Spread Function

The Gaussian intensity distribution illustrated in FIG. 1B is that of the combined illumination and light collection system 20 of FIG. 2. When system 20 is used to scan an object and to collect the light scattered thereby, the point spread function obtained has a similar shape as that shown in FIG. 1B. FIG. 1B therefore also illustrates the point spread function obtained when system 20 is used to scan and collect light scattered from an object. For this reason, in the description above, the curve in FIG. 1B is used to illustrate the data samples obtained by system 20 when scanning surface 40.

As discussed above in reference to FIGS. 1B, 1C above, the point spread function is a function of both x and y resolution element positions. In FIG. 2, the illumination system illuminates a small area of the surface 40 and the intensity distribution of such illumination essentially determines the point spread function of system 20.

Alternatively, in imaging type systems, such as those described in U.S. Pat. Nos. 4,532,650; 4,579,455; 4,805,123; and 4,926,489 referenced above, the illumination system illuminates a large area of the surface, and light from the surface to be inspected is focused by a light collection system in a manner similar to that of a camera. In such imaging systems, the design of the light collection system determines the point spread function of the combined illumination and light collection system. The point spread functions obtained using most such imaging systems also have Gaussian distributions of the form shown in FIG. 1B, and the above description concerning scanning and data acquisition can be generally applied to these imaging systems. Therefore, in both types of systems, when the intensity of the detected light is sampled, and when such sampled data is aligned prior to the detection and verification of anomalies, the characteristics of such point spread functions are taken into account as described in detail below. In other words, the data processing scheme described below, including the alignment to correct for misregistration process described below, is applicable to both types of systems.

Terminology and Setting for Data Processing

Anomalies are identified by comparing intensity levels or values from corresponding resolution element locations of images of adjacent instances of a repeating pattern—referred to as a strip unit (described below in detail)—on the wafer surface, where the repeating pattern may be a real one such as that of memory or logic devices on a semiconductor wafer. In the case of a non-patterned wafer, it is sometimes useful to define an imaginary repeating pattern; both types of patterns are referred to herein as repeating patterns, and strip units can be defined with respect to such repeating patterns. Scattered light data samples from corresponding locations of adjacent strip units are buffered and compared, where the data samples in which anomalies are being sought is referred to as the target array and the collection of reference data samples (against which the target array is compared) is referred to as the reference array.

The data processing portion of the system of this invention employs resolution elements of the order of several microns in size, which is considerably larger than the submicron resolution element size of the imaging type systems described above. Furthermore, in the preferred embodiment, by monitoring variations in the height of the surface to be inspected and correcting for such variations using an automatic positioning system such as that in U.S. Pat. No. 5,530,550, it is possible to achieve local data registration of better than ±1 resolution element in accuracy. These factors are exploited in the data processing design to enable less expensive and more efficient detection and verification of anomalies.

This invention employs strip-unit-to-strip-unit comparison (defined below) which assumes that the pattern on the wafer repeats in a periodic fashion. The fundamental repeating pattern unit on the wafer is a die and the two-dimensional spatial layout of die is called a die grid as shown in FIG. 5. In some instances, the fundamental repeating pattern may actually be a stepper field comprised of several die.

The data processing portion of the system is defined relative to the current strip scan (as shown in FIG. 4). The data processing coordinate system is defined by the scan axis X and sweep axes Y defined above in reference to FIG. 2 and has units of sweeps of the scan axis X and units of resolution elements along the sweep axis Y. The fundamental repeating pattern unit along a strip scan is denoted a strip unit. As shown in FIG. 6, the height h of a strip unit is defined as the height (length) of a sweep resolution element and the width d of a strip unit is defined as the width of a die. A strip unit may be comprised of several die and/or die segments as shown in FIG. 5 where a die segment is a portion of a die contained within a strip unit. Therefore, the height of a strip unit may contain exactly one dice, a segment of a dice, segments of two die, several whole die, or several whole die bounded by segments of one or two die. In the case of a non-patterned wafer, it is sometimes useful to define a virtual die and a corresponding virtual die grid, so that the definition of the strip unit above applies to non-patterned wafers as well. Seven strip units are shown in FIG. 6, where four of the units are labelled N−2, N−1, N, and N+1.

It is preferable for the illumination beam to be aligned with the real or virtual patterns on the surface inspected (e.g. with the "streets" between die patterns), so that the intensity values obtained by the light collection subsystem from adjacent patterns can be used for indicating anomalies. Such alignment is known to those skilled in the art and is discussed, for example, in U.S. Pat. No. 4,898,471 to Stonestrom et. al.

Data Processing Subsystem

FIG. 7 is a functional block diagram of the data processing subsystem 130 to illustrate the invention. During the scan of a surface, sweep generation by chirp generator 80 and data acquisition in the manner described above in reference to FIGS. 1A–6 are synchronized with data processing by timing signals that are generated by timing electronics 84. The timing signals from board 84 are, in turn, synchronized to the X-stage encoder 135. Therefore, as the illuminating beam sweeps the wafer surface, the collected light signal is digitized by the analog board 134 and passed to the data processing board 136 through the alignment board 138 for processing. In order to process the collected light signal from four collection channels independently, each channel has its own analog board and data processing board, where all channels derive their timing information from a common timing electronics board 84. The timing electronics board 84 controls, among other functions, the inter-sweep distance, strip-unit width, and the number of strip units that will be acquired. An automatic positioning system (not shown in FIGS. 2, 3) with electronics 99 such as that in U.S. Pat. No. 5,530,550 is also employed.

Data Processing Board 136

FIG. 8 is a block diagram showing in more detail the data processing board 136 of FIG. 7. Analog board 134 converts the intensity data from one of the collectors 110*a*, 110*b*, 111*a*, 111*b* to digitized data. The incoming digitized data from the analog and alignment boards is first stored in a data buffer 142 of a memory management unit 140 after a certain delay by delay element 144. The delay is to allow time for the board 136 to process the data stored in the buffer 142 before it is over-written by new incoming data. Memory management unit 140 supplies the buffered and incoming data to four parallel paths: two detection stages 152, 154 and two verification stages 162, 164.

In the preferred embodiment, the detection and verification stages are stream-based processing stages that process data at a rate substantially equal to the average sampling rate of the system. The sampling rate is in turn synchronized with the scan rate of the surface as noted above.

In reference to FIGS. 6 and 8, the sampling data acquired for strip unit N−1 is compared to the sampling data acquired during a number of previous sweeps for the strip unit N−2 and is also compared to the intensity data that will be acquired and forthcoming from memory management unit 140 for the strip unit N. In such comparison, the sampling data for the strip units N−2 and N are taken as the reference images for comparison with the target image in strip unit N−1. Where strip unit N is the target image, then units N−1 and N+1 are the respective reference images for comparison. Therefore, for each pair of strip units N−1, N, two comparisons are performed: one where N−1 is the target image and N is the reference image, and the other where N is the target image and N−1 is the reference image. After further processing by anomaly detection logic 172, 174 and the event processing stage 180, the results of the comparisons are supplied to the system Central Processing Unit (CPU) 131 of FIG. 7 to be combined with other comparisons for anomaly detection and verification. For example, the further processed result of the comparison where N is the target image and N−1 is the reference image is supplied to the system CPU. At a later point in time, the intensity data for the strip unit N+1 is acquired and received by board 136 and is then used as a reference image to be compared to the target image in strip unit N. The further processed result of such comparison is also supplied to the system CPU to be combined with the result of comparison where N is the target image and N−1 is the reference image for anomaly detection and verification.

The outputs of the detection and verification stages 152, 162 are supplied to anomaly detection logic 172 for determining the presence of anomalies in strip unit N. In the same vein, detection and verification stages 154, 164 supply their outputs to anomaly detection logic 174 for determining the presence of anomalies in strip unit (N−1). The outputs of the detection logic 172, 174 are then processed by an event processing stage 180 which detects and characterizes events, where an event is defined as a connected region of (verified) anomalous resolution elements. The event processing stage 180 buffers events data and signals the availability of event data to the system CPU 131 through a download FIFO 182.

In the preferred embodiment, a resolution element is considered anomalous if the difference between its sampling data value (i.e. intensity value) and that of the corresponding resolution element in the neighboring strip unit exceeds the expected variation due to system errors. A verification stage verifies the anomalous resolution elements in order to remove false-positives. In the detection and verification processes described above, proper registration of data samples to the corresponding locations on the wafer surface is important. In the strip unit to the strip unit comparison employed in the detection verification processes, it is assumed that the delay introduced by delay element 144 would cause the resolution elements in a strip unit to be compared to those in an adjacent strip unit, such as strip unit N to strip unit N−1. The detection and verification processes described above compare the data samples acquired for the strip unit N to those acquired for strip unit N−1. If the data samples of either one or both strip units are misaligned or misregistered with respect to the resolution units in such strip unit, this will introduce an error in the comparison process. As noted above, by means of the automatic positioning system in U.S. Pat. No. 5,530,550 as well as other design features, it is possible to achieve local data registration of better than ±1 resolution element in accuracy. With the further shrinking of semiconductor devices to smaller sizes, it would be desirable to be able to achieve better data registration accuracy. The invention of this application achieves such goal.

The above detailed description in reference to FIGS. 1–8 is largely taken from the parent application.

FIG. 9 is a schematic top view of a semiconductor wafer having a two-dimensional array of locations relative to fast scan direction (direction of speed of the AOD) and a slow scan direction to illustrate the invention. As described above in reference to FIG. 1C, data samples collected correspond to the resolution elements such as resolution element P. For simplicity, such resolution elements are represented as dots 202 on the wafer 40. Alternatively, the dots 202 may be thought of as the center points of the resolution element, such as center point $P_c$ of resolution element P in FIG. 1C, where the center point is at the same distance from opposing sides of the rectangle of the corresponding resolution element. For simplicity, each resolution element or its center point is referred to as a location herein.

Therefore, the locations 202 on wafer 40 form a two-dimensional array of rows and columns, such as row 204 and column 206. In the preferred embodiment, the rows of locations are along the fast scan direction of the sweep, that is, along the Y axis, while the columns and the slow scan direction are along the X axis.

As described above, a data sample is acquired for each location on wafer 40 so that the data samples acquired corresponding to the locations also form a two-dimensional array of rows and columns. In the preferred embodiment, each row or a portion thereof forms a vector; it being understood that any one dimensional group of data samples may be defined as a vector, such as those in a column (e.g. column 206), or ones in a diagonal direction. Furthermore, the data samples in a group need not be all contiguous to one another; in other words, it is possible to exclude one or more data samples from a row, column or diagonal array of data samples from a group if desired. Thus, misregistration of the data samples with respect to the corresponding locations on the wafer would cause errors in anomaly detection and verification. One of the goals of this invention is to reduce such misregistration errors by misregistration correction. Since the point spread functions obtained using most illumination and detection optical systems are smooth and symmetrical, the data samples acquired from neighboring locations are usually highly correlated and this fact can be exploited in misregistration correction.

One aspect of the invention is based on the observation that, for each vector, a reference vector may be formed by averaging vectors adjacent to the current vector being processed and then adjusting the locations of the data samples in the current vector by comparing the current vector to the reference vector in order to correct misregistration errors. This is illustrated in FIG. 10A.

FIG. 10A is a schematic view of a current vector at the ith row and eight adjacent vectors of the current vector in reference to a coordinate system to illustrate the above described aspect of the invention involving a reference vector. Each horizontal line in rows (i−4) through (i+4) represents a vector (i.e. data samples along the row). Each vector may comprise the data samples acquired in a sweep as shown in FIGS. 2 and 4 or a portion of such data samples. This invention is equally applicable to inspection systems where the beam for illumination scans across the entire wafer surface in one scan, so that a vector may comprise data samples corresponding to locations across the entire wafer surface.

In order to increase the accuracy of anomaly detection and verification, it is desirable to first pre-process the data samples acquired to correct for misregistration errors and then supply the data samples after such correction to the detection and verification stages 152, 154, 162, 164 in FIG. 8 for anomaly detection and verification. The vectors in FIG.

10A represent data samples acquired after digitization, prior to misregistration correction and before they are sent to the detection and verification stages. The current vector at the ith row has a number of adjacent vectors as shown in FIG. 10A. As illustrated by the point spread function 210 obtained using an illumination and collection system such as system 20, the adjacent vectors at the (i−1)th through (i−3)th rows and the adjacent vectors at the (i+1)th through (i+3)th rows are highly correlated with the current vector at the ith row and this fact can be exploited for misregistration correction. A reference vector may be formed by taking the average of the eight rows, (i−3)th through (i+4)th. Thus, the data sample at the ith row and jth column of the reference vector for the above described current vector on the ith row may be formed by taking an average of the data samples at the jth column in the eight vectors at the (i−3)th through (i+4)th rows. Preferably, a weighted average of the data samples are taken, where the weighting coefficients preferably vary with the point spread function 210 obtained using the optical illumination/collection system. In the preferred embodiment, the reference vector G is given by:

$$G_{i,j} = \sum_{q=-H/2}^{H/2-1} D_q Y_{(i+q),j} \quad (1)$$

where $Y_{i,j}$ is the data sample value at the ith row, jth column of the two-dimensional array of data samples; $D_q$ are weighting coefficients; H is the number of selected vectors for generation of the reference vector; $G_{i,j}$ is the value of the reference vector at the ith row and jth column of the two-dimensional array; where j ranges from N/2 to −N/2 so that the current vector being processed, the reference vector and selected vectors each has N data samples. Preferably N ranges from 512 to 8192. Thus, in the example above, H is 8.

By comparing the current vector with the reference vector so formed, it is possible to correct for misregistration errors. In the above described scheme, however, by taking an average over vectors at different rows to form the reference vector, one would correct for misregistration errors that are in the slow scan direction X but not misregistration errors in the fast scan direction Y. To correct for misregistration errors in the Y direction also, in the preferred embodiment, each of the data samples in the current vector is compared, not just with the corresponding data sample of the reference vector in the same column, but also with the data samples in the reference vector in adjacent columns. In this comparison process, the best fit is found. If the best fit calls for repositioning the data sample to a different column, such data sample in the current vector is then repositioned to correct for misregistration errors. This comparison process may be implemented through normalized crosscorrelation or normalized residual minimization described below.

Another factor involved in misregistration correction is that the background reflectivity of the surface independent of any anomaly may vary across the surface due to effects such as process variations, and such variation may interfere with the above-described process for misregistration correction. Therefore, to reduce the effects of such local variations, in the preferred embodiment, for each data sample in the current vector being processed, an average value for the data samples in the current vector and an average value for the data samples in a reference vectors are computed. Preferably, the data samples in the current vector and in the reference vector from which the averages are computed are centered at the data sample in the current vector being processed. The difference between each of the data samples in the current and reference vectors and their respective average values then define respectively a residual current vector and a residual reference vector. This averaging process is illustrated in FIG. 10B described below.

FIG. 10B is a schematic view of data samples in a reference vector to illustrate the process for generating a local average vector and residual reference vector from raw data. The dots in FIG. 10B refer to locations, or center points (e.g. $P_c$ in FIG. 1C) of resolution elements, and the values such as G(1,5) refer to the data samples detected at such resolution elements or locations. In order to generate the local average, the user needs to decide a window for generating the average value. The size of the window should be such that by averaging over the window, variations in the reflected intensity due to different reflectivities across the surface are reduced or eliminated. Thus, for example in FIG. 10B, the local average value $\overline{G}_{i,5}$ for the data sample at the ith row and the fifth column may be obtained by obtaining an average of eight data samples from the data sample $G_{i,1}$ in the first column through the data sample $G_{i,8}$ in the eighth column, all on the ith row, so that the averaging window A is eight. The above described averaging process is illustrated by the equation (2) below:

$$\overline{G}_{(i,5)} = \frac{1}{8} \sum_{n=-\frac{8}{2}}^{\frac{8}{2}-1} G_{(i,n+5)} \quad (2)$$

$$G_{R(i,5)} = G_{(i,5)} - \overline{G}_{(i,5)} \quad (3)$$

In order to reduce the effects of the variations of reflectivity of the surface, the above average value is then subtracted from the data sample to obtain a residual data sample $G_{R(i, 5)}$ at the ith row and fifth column in the equation (3) above. This process is repeated for other locations and the resulting vector is referred to as a residual vector.

The above described process may be performed for each data sample in each reference vector as well as in each current vector to yield residual current and reference vectors. The processes of crosscorrelation and residual minimization will now be illustrated in reference to FIG. 10C.

FIG. 10C shows a residual reference vector and a residual current vector for illustrating the crosscorrelation and residual minimization processes of this invention. Both the residual reference vector $G_{R(i)}$ and the residual current vector $Y_{R(i)}$ on the ith row are shown in FIG. 10C. When the data samples in the residual current vector $Y_{R(i)}$ are compared to those in the residual reference vector $G_{R(i)}$, one possible comparison is to compare each data sample at location (i,j) of $Y_{R(i)}$ to the data sample at the same location (i,j) in $G_{R(i)}$. If the data samples in the residual current vector are misregistered in the ±Y direction, however, there is likely to be a discrepancy between the data sample in the residual current vector at location (i,j) and the data sample in the residual reference vector at that location. This discrepancy can be detected by comparing data samples in the residual current vector also to data samples that are offset in the ±Y direction from such data samples in the residual reference vector.

Thus, if the data sample at the resolution element location (i, 16) of the residual current vector is being processed, such data sample is compared not only to the data sample at the same location in the residual reference vector, but also to data samples at neighboring locations such as (i, 15), (i, 14) and (i, 17). In order to determine whether the data sample in the residual current vector at (i, 16) is to be repositioned, not only is the data sample at such location in the current vector compared to data samples in the residual reference vector, but preferably also data samples in the neighboring locations such as (i, 14), (i, 15) and (i, 17) in the current vector are also compared to data samples that are offset by the same number of locations in the residual reference vector to exploit the high correlation between adjacent data samples. From this comparison process, it is then determined whether the data sample in the residual current vector at (i, 16) is misregistered and whether it should be repositioned. The comparison can entail a crosscorrelation or residual minimization process, or other similar or equivalent processes.

The preferred embodiment employs crosscorrelation. In one example illustrated in FIG. 10C, in order to determine whether the data sample at (i, 16) should be repositioned, four data samples at locations (i, 14) through (i, 17) in the residual current vector are crosscorrelated with a plurality of sets of four data samples in the residual reference vector to yield a plurality of crosscorrelation coefficients, each set having a different offset m in the ±Y direction relative to the data samples of the residual current vector. Thus, where the offset variable m is −2 as shown in FIG. 10C, the set of four data samples in the residual current vector at locations (i, 14) through (i, 17) are crosscorrelated with the four data samples in the residual reference vector at locations (i, 12) through (i, 15) to yield a crosscorrelation coefficient. This is performed by multiplying corresponding pairs of data samples connected by arrows 220, and summing the four products to obtain the sum $G_{R(i, 12)}Y_{R(i, 14)} + G_{R(i, 13)}Y_{R(i, 15)} + G_{R(i, 14)}Y_{R(i, 16)} + G_{R(i, 15)}Y_{R(i, 17)}$. This sum of the four products is divided by the product of the square root of the sum of squares of $G_{R(i, 12)}$, $G_{R(i, 13)}$, $G_{R(i, 14)}$, $G_{R(i, 15)}$ with the square root of the sum of squares of $Y_{R(i, 14)}$, $Y_{R(i, 15)}$, $Y_{R(i, 16)}$, $Y_{R(i, 17)}$. This expression is given in the equation below:

$$C_{i,16}(-2) = \frac{\sum_{n=-2}^{1} G_{R(i,16-2+n)} Y_{R(i,16+n)}}{\sqrt{\sum_{n=-2}^{1} G_{R(i,16-2+n)}^2} \sqrt{\sum_{n=-2}^{1} Y_{R(i,16+n)}^2}} \quad (4)$$

In equation (4) above, the crosscorrelation coefficient $C_{i,16}(-2)$ is for the data sample at location (i, 16) for the offset m of −2.

The crosscorrelation process is illustrated by the four arrows 220 in FIG. 10C. If the offset is −1 instead, then the four data samples in the residual current vector at locations (i, 14) through (i, 17) will be crosscorrelated with the data samples at locations (i, 13) through (i, 16) in the residual reference vector as illustrated by arrows 222 in dotted lines. Of course these same four data samples in the residual current vector may be crosscorrelated with the data samples at the same four locations (i, 14) through (i, 17) of the residual reference vector where there is then no offset (m=0) between the two sets of data samples.

The above process may be repeated with different offsets to the extent necessary or desired to cover the expected extent of misregistration errors. In other words, if the data sample at (i, 16) is not expected to be misregistered by more than two resolution elements in the −Y and +Y directions, then there is no need to perform the crosscorrelation process at offsets more than two resolution elements from (i, 16). There is then no need for the offset m to be less than −2 or greater than +2, so that a total of five crosscorrelation processes with five different offset values would be adequate. If, for example, the five crosscorrelation processes are carried out with the offset m being equal to −2, −1, 0, +1, +2, then the entire process would result in five crosscorrelation coefficients. The highest one of the five crosscorrelation coefficients corresponding to an offset m would indicate that there is maximum correlation between the residual reference vector with such offset and the residual current vector.

In the example of FIG. 10C, if it turns out that the crosscorrelation coefficient where the offset m has the value −2 is the maximum of the five, this means that the data sample at location (i, 16) has been misregistered by 2 resolution elements in the −Y direction so that in order to correct for misregistration error, such data sample should be repositioned at location (i, 14).

The crosscorrelation window W is chosen based on an estimate on the extent of correlation of the data samples in the neighborhood of the location (i, 16). The number illustrated in FIG. 10C, namely four, corresponds to the number of resolution elements along the Y direction in the illuminated spot 10 in FIG. 1C. Obviously, a number greater than four or less than four may be chosen to be the crosscorrelation window, and the number can be even or odd. All such variations are within the scope of the invention.

Therefore, in general, the crosscorrelation coefficient for the data sample at the ith row and jth column at offset m may be obtained by the equations below:

$$\overline{Y}_{i,j} = \frac{1}{A} \sum_{p=-A/2}^{A/2-1} Y_{i,(j+p)} \quad (5)$$

$$\overline{G}_{i,j} = \frac{1}{A} \sum_{p=-A/2}^{A/2-1} G_{i,(j+p)} \quad (6)$$

where A is a size of a window within which averaging is performed; and $\overline{Y}_{i,j}$, $\overline{G}_{i,j}$ are the averaged values of $Y_{i,j}$, $G_{i,j}$ within the window of width A;

$$C_{i,j}(m) = \frac{\sum_{l=-W/2}^{W/2-1} (G_{i,(j+l+m)} - \overline{G}_{i,(j+l+m)})(Y_{i,(j+l)} - \overline{Y}_{i,(j+l)})}{\sqrt{\sum_{l=-W/2}^{W/2-1} (G_{i,(j+l+m)} - \overline{G}_{i,(j+l+m)})^2} \sqrt{\sum_{l=-W/2}^{W/2-1} (Y_{i,(j+l)} - \overline{Y}_{i,(j+l)})^2}}$$

where $C_{i,j}(m)$ is a crosscorrelation coefficient at the ith row and jth column when the reference vector is in the same row but offset by m data samples relative to the at least one vector; and W is a size of a correlation window for the crosscorrelation coefficient.

The number of data samples in each vector may be in the range of 512 to 8192. The crosscorrelation window W may be in the range of about 4 to 64.

This process is then repeated for each data sample in the current vector until all of the data samples in the current vector have been re-positioned where necessary to correct for misregistration errors.

FIG. 11 is a block diagram illustrating how the crosscorrelation process may be implemented. The functions in FIG. 11 may be implemented in hardware or as processing steps in a microprocessor, on the alignment board 138 in FIG. 7. As shown in FIG. 11, the scattered intensities from the locations 202 of FIG. 9 detected by the detectors 110a, 110b, 111a, 111b of FIG. 3 are digitized by the analog board 134 of FIG. 7 and supplied to the alignment board 138. Such data are then fed to two parallel path inputs 252, 254 of FIG. 11 as the inputs for the current vector and reference vector. The input digital data are stored in corresponding data buffers 256, 258 in the two paths.

For each data sample $Y_{i,j}$ (at the resolution element location (i,j) of the current vector) input to the current vector data input 252, the calculation below is performed to determine whether such sample needs to be repositioned in order to correct for misregistration errors relative to such resolution element. The running average of data samples in the row of the vector is computed for both the current vector and the reference vector by corresponding generators 262, 264 in accordance with equations (5) and (6) above over an averaging window A in the manner described above in reference to FIG. 10B. These averages are computed for each data sample $Y_{i,j}$, $G_{i,j}$. The running average for such data sample in the current vector is then supplied to block 266 which computes residual data samples by subtracting from each data sample in the current vector the running average value computed by block 262 to arrive at a residual current vector. Block 268 performs a similar operation for deriving a residual reference vector.

The residual current vector and the residual reference vector are delayed respectively by delays 272, 274. As described above in reference to FIG. 10C, in computing the crosscorrelation coefficient, each residual data sample in the residual current vector is multiplied by a corresponding residual data sample in the residual reference vector. If there is no offset between such two residual data samples that are multiplied, then the delays introduced by blocks 272, 274 may be substantially the same. In such event, the outputs of blocks 272, 274 would supply residual data samples from the residual current vector and residual reference vector obtained for the same resolution element location to multiplier 286 for deriving the product of the two residual data samples. The product is then stored in block 286 for addition to other similar products. If, however, there is to be an offset between the two residual data samples (from blocks 266, 268) of the residual current and reference vectors that are multiplied, the two blocks 272, 274 will introduce different delays so that residual data samples with the appropriate offset there between from the two residual vectors are multiplied by multiplier 286.

For achieving a negative offset (m being negative), block 274 introduces a delay greater than that introduced by block 272; for achieving a positive offset (m being positive), block 272 introduces a delay greater than that introduced by block 274. Both positive and negative offsets may be implemented by a fixed delay in block 274 and a variable delay in block 272. The products of corresponding pairs of data samples in the two residual vectors are then added in block 286 over the crosscorrelation window W as described above to arrive at a value for the numerator in equation 7 for the crosscorrelation coefficient for a particular value of the offset m.

Blocks 276, 278 generate respectively the squares of the residual data samples that are in the window W in the residual current vector and the squares of the residual data samples that are in the window W in the residual reference vector respectively. Blocks 282, 284 compute respectively, the square root of the sum of the squares from blocks 276, 278 respectively. The two square roots are multiplied by multiplier 288 to arrive at the denominator in equation 7. The numerator and denominator are then divided by divider 290 to provide a value for the crosscorrelation coefficient at offset m.

The above described process is repeated for different values of offset m to provide a crosscorrelation coefficient corresponding to each of a plurality of different values of the offset m and block 292 determines, from this plurality of crosscorrelation coefficients, the one value ($m_{max}$) that is maximum of m. This value $m_{max}$ of m corresponding to such crosscorrelation coefficient is then determined by block 294 and this controls the variable delay block 296 to introduce the appropriate amount of delay so that the data sample in the current vector from input 252 will be repositioned, if necessary, from location (i, j) to (i, j+$m_{max}$) and this data sample is then stored in a register. After being delayed by a fixed delay 298, the reference vector data is stored in a register also.

FIG. 12 is a block diagram illustrating a system for correcting misregistration to illustrate an alternative embodiment of the invention employing residual minimization. Instead of or in addition to the crosscorrelation process described above in reference to FIG. 11, misregistration errors can also be corrected by means of a residual minimization process illustrated in FIG. 12. The residual minimization process of FIG. 12 again may be implemented in hardware or by processing steps of a microprocessor. In the embodiment of FIG. 11, the effects of different reflectivities across the surface is reduced by deriving an average for the reference vector and the current vector and subtracting such average from each data sample to obtain a residual reference vector or residual current vector. In the embodiment of FIG. 12, in contrast, such effects are reduced by generating a local average value of the data samples surrounding a data sample in a reference vector or current vector and dividing each data sample or a signal derived therefrom in the current vector or reference vector by such average to derive a normalized reference vector or current vector.

Thus as shown in FIG. 12, a stream of digitized data samples from the analog board 134 is supplied to inputs 302, 304 and buffers 306, 308. Block 312 then generates a local average for each data sample in the current vector from data samples in the vicinity of such data sample. Preferably, the data samples from which the average is derived surrounds such data sample and enough neighboring data samples are included in the averaging process to reduce errors caused by variations in reflectivities across the surface. The data sample in the current vector or a signal derived therefrom is then divided by such average to yield a normalized data sample. This process is performed for all the data samples in the current vector so that a normalized current vector is supplied by block 316 to delay 322.

Blocks 314, 318 perform functions similar to those of blocks 312, 316 so that block 318 supplies a normalized reference vector to delay 324. Delays 322, 324 function in substantially the same manner as blocks 272, 274 of FIG. 11 to introduce no relative delay or a desired relative delay there between and therefore no offset or a desired data sample offset between the normalized current vector and the normalized reference vector. Each normalized data sample within a window (similar to the window W in the embodiment of FIG. 11 and equation 7 above) in the normalized reference vector is subtracted from a corresponding normalized data sample in a window in the normalized current vector by subtractor 326 to arrive at a difference value for each data sample within the window in the normalized current vector. The absolute values of such differences are added together by block 328 as a residual value for the current vector and this residual value is supplied to block 330.

The above described process is repeated for different values of the offset between the normalized reference and normalized current vectors in order to generate a number of different residual values, each corresponding to a different offset in a manner similar to that described above in reference to FIG. 11. Block 330 detects which of these residual values is the minimum and the offset value corresponding to it. This offset value is then supplied to variable delay 332 for delaying the normalized data sample of the current vector so as to reposition the normalized data sample in order to correct for misregistration errors. This process is then repeated for some or all of the data samples in the current vector.

FIG. 13 is a schematic view illustrating a normalization process, such as the one described above in reference to FIG. 12. As shown in FIG. 13, in order to normalize the data sample at the resolution element location on the ith row and jth column, it may be desirable to obtain an average of 16 data samples with locations (marked by X in FIG. 13) ranging from (j−2) to (j+1) in the Y direction and (i−2) to (i+1) in the X direction. For this purpose, blocks 312, 314 preferably generate average values by adding the 16 data samples and dividing the sum by 16 and provide such average value to block 316 or 318. Divider blocks 316, 318 preferably subtract from the sum a fraction of the average data sample value, and divide the difference by the average to obtain a normalized data sample value. Two equations similar in form to the one just described are equations (9) and (10) shown below.

Strip Unit To Strip Unit Comparison

In lieu of, or in addition to, the above described embodiments for misregistration correction using a reference vector, another scheme for misregistration correction makes use of the fact that there may be repeating patterns on the surface to be inspected so that these repeating patterns can be exploited for aligning the data samples with locations on the surface to correct misregistration errors, in a scheme analogous to the strip unit comparison described above in reference to FIGS. 6 and 8. Thus, if strip unit N is thought to contain the same pattern as strip unit N−1, the data samples in strip unit N may be used as a reference and compared to the data samples in strip unit N−1 for detecting misregistration errors. Therefore, instead of supplying digitized data from the analog board 134 from essentially the same locale on the surface to be inspected as in th schemes of FIGS. 11 and 12, digitized data samples collected from different locales thought to contain the same pattern may be used for comparison, the data samples from one locale referred to as a reference array and the data samples from the other locale referred to as a target array.

FIGS. 14A–14D and 15 illustrate a normalization and residual minimization process for misregistration correction by comparing the target and reference arrays. FIG. 14A is a schematic view of a two-dimensional array of data samples and a target subarray 340 taken from the two-dimensional array in one of the strip units, such as strip unit N of FIG. 6. FIG. 14C is a schematic view of a two-dimensional subarray 342 of data samples taken from a two-dimensional array of data samples in a reference strip unit, such as strip unit N−1 in FIG. 6. From each of the two subarrays in FIGS. 14A and 14C, a local average data sample value may be derived at each of the locations in the two subarrays 340, 342, and in other subarrays, except at the edges of the arrays. In a process similar to that described above in reference to FIG. 13, for example, the local average value at the location (3, 3) may be derived by adding the data samples that are in the first row through the fourth row and in the first column through the fourth column, or a total of sixteen data samples, and dividing the sum by 16 in the equation given below:

$$\overline{T}_{(3,3)} = 1/(16)*[T_{(1,1)} + T_{(1,2)} + T_{(1,3)} + T_{(1,4)} + T_{(2,1)} + T_{(2,2)} + T_{(2,3)} + T_{(2,4)} + T_{(3,1)} + T_{(3,2)} + T_{(3,3)} + T_{(3,4)} + T_{(4,1)} + T_{(4,2)} + T_{(4,3)} + T_{(4,4)}] \quad (8)$$

for the target subarray. The local average value for the location (3, 3) is labelled $\overline{T}_{(3,3)}$ and similar local averages may be derived at other locations in the subarray for both the target subarray and the reference subarray. The arrays of local average values derived in this process are shown in FIGS. 14B and 14D. Preferably, the subarrays in FIGS. 14A and 14C are large enough so that the edge effects do not significantly affect the accuracy of the misregistration correction process; for this reason, the subarrays are preferably much larger than as shown in FIGS. 14A, 14C.

As shown in FIG. 15, the data samples for the target subarray and for the reference subarray are fed respectively to inputs 352, 354 and are stored respectively in memory buffers 356, 358. Local averages are generated in the manner described above in reference to FIGS. 13 and 14A–14D by blocks 362, 364. Then, the data sample at each location in the subarray is divided by the local average value derived for such location by blocks 366, 368 to obtain a normalized subarray of target subarray data samples at the output of block 366 and a subarray of normalized reference data samples at the output of block 368. In the preferred embodiment shown in FIGS. 14A, 14C, subarray 342 of the reference array corresponds to the same resolution element locations as target subarray 340 and defines a reference position of the reference subarray; it will be understood that other reference subarrays may also be used to be the reference position for the reference position. The remaining reference subarrays that are to be compared to the target subarray are then offset relative to the reference position by at least one row and/or column.

In the same manner to that described above by reference to FIGS. 11 and 12, in the preferred embodiment, if there is to be no offset between the data samples of a reference subarray and the reference position, blocks 372, 374 would introduce the same amount of delay. Thus, for target subarray 340, reference subarray 342 comprising data samples at corresponding locations in the reference array to the target array preferably defines the reference position. In the event that a subarray other than subarray 342 is used for comparison (i.e. a reference subarray that is offset from the reference position), then blocks 372, 374 introduce different relative delays between target subarray 340 and such selected different reference subarray. The subtract block 376 would subtract from each data sample in the normalized target subarray the data sample at the corresponding location from the selected normalized reference subarray to obtain a difference value which is supplied to block 378. Block 378 stores such difference values for each of the locations of the target subarray and computes a sum of the absolute values of the differences from the output of block 376. This sum is then supplied to block 380.

The above process is then repeated where there is a different offset between the reference subarray and the reference position by one or more columns in the Y direction, where the offset m is the offset of the number of columns. As in the case of the reference vector comparison, the range of value for m in this context is also chosen to be the maximum expected range of misregistration errors. Thus, if the misregistration error in the Y direction is not expected to exceed two resolution elements in the −Y or +Y directions, then the value of m should be chosen to range from −2 to +2. In such event, the delays introduced by blocks 374, 372 are chosen such that the block 378 computes the sums by reference to a reference subarray that is offset from the reference position by one of the five relative offset values m in the ±Y direction.

Different from the case of the current and reference vectors, the reference subarrays may also be misregistered relative to the reference position in the X direction so that another offset variable n is used to track the offset in the X direction. In such event, a number of reference subarrays, each offset from the reference position by at least one row (n) and/or column (m), may be compared to the target subarray to correct for misregistration errors. Thus if both m and n are —1, the subarray 340 will be compared to the subarray 344 in FIG. 14C. In the same vein, if misregistration errors in the X direction are not expected to exceed one resolution elements in the −X and +X directions, then n may take on one of the three values: −1, 0, +1. Again, the delays introduced by blocks 372, 374 are adjusted to achieve such relative offsets. Thus, if both m and n are expected to range from −1 to +1, the above described process for deriving the sum of absolute values of the differences would be repeated 9 times corresponding to 9 combinations of different values (3 each) of m and n. Such 9 sums are then supplied to block 380 which detects which of the 9 values is minimum. Such minimum residual value and the offset values for m and n of the reference subarray that give rise to such minimum residual value would indicate the best match between the reference and target subarrays. In order to correct the misregistration errors, such offset values for m and n are then supplied to variable delay block 382 which delays the normalized target subarray by the appropriate amount so as to correct for misregistration errors.

In the preferred embodiment, in a normalization process in blocks 362, 366 and 364, 368, it may be desirable to first subtract from each data sample in the target subarray and reference subarray a certain percentage of the local average value to obtain a difference and then dividing such difference by the average value to obtain a normalized data sample value. The normalization processes above may be performed by the following equations:

$$R^N_{i,j} = \frac{R_{i,j} - \alpha_R \overline{R}_{i,j}}{\overline{R}_{i,j}} \tag{9}$$

$$T^N_{i,j} = \frac{T_{i,j} - \alpha_T \overline{T}_{i,j}}{\overline{T}_{i,j}} \tag{10}$$

$$0 \leq \alpha_R \leq 1 \tag{11}$$

$$0 \leq \alpha_T \leq 1 \tag{12}$$

where
$R^N_{i,j}$, $T^N_{i,j}$ are the normalized values respectively of the data samples at the ith row and jth column of the reference and target subarrays, $R_{i,j}$, $T_{i,j}$ are the values respectively of the data samples at the ith row and jth column of the reference and target subarrays, $\alpha_T, \alpha_R$ being weighting factors, and $\overline{R}_{i,j}$, $\overline{T}_{i,j}$ are local averaged values of the data samples at the ith row and jth column over the reference and target subarrays respectively that are given by:

$$\overline{R}_{i,j} = \frac{1}{K^2} \sum_{l=\frac{-K}{2}}^{\frac{K}{2}-1} \left( \sum_{m=\frac{-K}{2}}^{\frac{K}{2}-1} R_{(i+l),(j+m)} \right) \tag{13}$$

$$\overline{T}_{i,j} = \frac{1}{K^2} \sum_{l=\frac{-K}{2}}^{\frac{K}{2}-1} \left( \sum_{m=\frac{-K}{2}}^{\frac{K}{2}-1} T_{(i+l),(j+m)} \right) \tag{14}$$

where
K is size of an averaging window.

The operation carried out by blocks 376, 378 are given by:

$$H_{n,m} = \sum_{i=0}^{M-1} \sum_{j=0}^{N-1} |T^N_{(i+n),(j+m)} - R^N_{i,j}| \tag{15}$$

where

M is the number of data samples in each column of the reference and target subarrays;

N is the number of data samples in each row of the reference and target subarrays;

m is the number of columns by which the reference subarray is offset from the reference position, where m can be zero;

n is the number of rows by which the reference subarray is offset from the reference position, where n can be zero; and H(n,m) is the residual value corresponding to a reference subarray that is shifted by n rows and m columns from the target subarray.

The effect of normalization illustrated in FIGS. 13 and 14A–14D are illustrated in FIGS. 16A and 16B. FIG. 16A is a graphical plot of an unnormalized and a normalized data vector A obtained from a surface of object 40 of FIG. 2 inspected having a relatively uniform background reflectivity. FIG. 16B is a graphical plot of a normalized and an unnormalized data sample vector B of a surface of object 40 inspected where the background reflectivity varies across a portion of the surface. In FIGS. 16A and 16B the unnormalized vectors A, B are shown in solid lines 388, 390 and the normalized vectors are shown as dotted lines 392, 394. As shown in FIGS. 16A and 16B, where the reflectivity of the surface varies across the surface, the normalization process will reduce errors caused by such variations.

FIG. 16C is a graphical plot of the normalized sums of residuals versus one of the offsets n, m. By determining the offsets n, m that give rise to a minimum residual value from the plot, misregistration errors can be reduced or eliminated. FIG. 16C illustrates the situation where the residual value is minimum with m or n being zero.

FIGS. 16D and 16E are respectively, computer plots of the data samples in a reference array and those in a target array. As can be seen from the two plots, both arrays contain scattering by patterns on the surface. FIG. 16F is a computer plot of residual data samples in the target array and FIG. 16G is a computer plot of the data samples from FIG. 16F but after such data samples have been repositioned for misregistration correction.

FIG. 17 is a block diagram for implementing normalized crosscorrelation of a target subarray with a reference subarray to illustrate another aspect of the invention. The operation in FIG. 17 is analogous to that of FIG. 11 for normalized crosscorrelation of a current vector with a reference vector, except that in FIG. 17, system 400 operates on a target subarray instead of a current vector and on a reference subarray instead of a reference vector. Thus, buffers 406, 408 would store respectively the target array and subarray and reference array and subarray data samples respectively. Generators 412, 414 would generate the average values $\overline{T}_{i,j}$, $\overline{R}_{i,j}$ according to equations 13 and 14 above and blocks 416 and 418 would calculate the normalized target and reference subarray values in accordance with Equations 9–12 above. The remaining blocks of FIG. 17 then perform essentially the same functions as those of blocks 272–290 of FIG. 11 to obtain a plurality of crosscorrelation coefficients provided to block 442, where each coefficient corresponds to a different pair of values n, m. Block 442 then selects the maximum crosscorrelation coefficient and identifies the pair of values of n, m, that gives rise to such maximum crosscorrelation coefficient. In response to such pair of values, block 444 then derives a control signal for controlling the amount of delay to be applied by block 446 in order to reposition the data samples in the target subarray where necessary to correct for misregistration errors.

The operation performed by blocks 426 through 440 are illustrated by equation 16 below which is analogous to the equation 7 above:

$$C_{i,j}(n, m) = \frac{\sum_{o=-\frac{V}{2}}^{\frac{V}{2}-1} \sum_{p=-\frac{W}{2}}^{\frac{W}{2}-1} T^N_{(i+n+o),(j+m+p)} R^N_{(i+o),(j+p)}}{\sqrt{\sum_{o=-\frac{V}{2}}^{\frac{V}{2}-1} \sum_{p=-\frac{W}{2}}^{\frac{W}{2}-1} \{T^N_{(i+n+o),(j+m+p)}\}^2} \sqrt{\sum_{o=-\frac{V}{2}}^{\frac{V}{2}-1} \sum_{p=-\frac{W}{2}}^{\frac{W}{2}-1} \{R^N_{(i+o),(j+p)}\}^2}} \quad (16)$$

Where m is the number of columns by which the reference subarray is offset from the reference position, where m can be zero;

n is the number of rows by which the reference subarray is offset from the reference position, where n can be zero; and W is the crosscorrelation window in the ±Y direction and V is the crosscorrelation window in the ±X direction.

Again, the number of data samples in each row or column of an array may be in the range of 512 to 8192 and the crosscorrelation windows W, V may be in the range of about 4 to 64.

In some applications, it may be desirable to process more data samples than are actually acquired. Additional data can be produced by a process of interpolation. This is illustrated in FIG. 18. Thus, as a part of the analog board 134 of FIG. 7 or a part of the alignment board 138 of the same figure, a two-dimensional interpolation function may be employed for deriving a larger output data sample array than the input array. If the input array has M rows and N columns of data samples, the output of block 450 may contain KM rows and LN columns of data samples, where K, L are positive integers. The data samples in the output array of block 450 are then input to the system shown in FIGS. 11, 12, 15 and 17.

Adaptive Illumination

In an in-line high speed wafer inspection tool, an important factor which limits the detection sensitivity of the instrument is the background scattering from patterns that are present on the wafer surface. This background can vary over four orders of magnitude and it is in the presence of this background that the relatively small signals from anomalies of interest have to be detected. Despite careful selection of the illumination/collection polarization as well as spatial filtering to reduce the background, such background can still vary over too large a dynamic range, requiring complex and expensive electronics and data processing to extract the anomalies of interest. Thus, another aspect of the invention is directed to the observation that the dynamic range of background signal can be much reduced by adaptively modulating the intensity of the illuminating beam in response to the output of a detector detecting the specular reflection or scattering from the surface.

FIG. 19 is a system diagram illustrating a portion of system 20 of FIG. 2 to illustrate the aspect of the invention on adaptively modulating the intensity of the illuminating beam. As shown in FIGS. 2 and 19, detector 90 detects the specular reflection of beam 38 from surface 40. An integrator 502 integrates the intensity signal across a line of sweep 50 across the surface and peak detector 504 detects the peak intensity detected during such sweep. The integrated intensity and the peak intensity are converted to digital signals by converter 506 and supplied to a digital signal processor 510. In response to the integrated intensity from integrator 502 and the peak intensity from 504, the digital signal processor supplies a control signal for controlling the attenuation to be applied by attenuator 512. This output of the processor 510 is converted by digital to analog convertor 514 before the signal is applied to attenuator 512. Attenuator 512 attenuates the output of chirp generator 520 before the generator output is applied to amplifier 82 which, in turn, powers the AOD 30. By reducing the voltage that is applied to the AOD 30 when the specular reflection intensity detected by detector 90 is high and increasing such voltage when the detected intensity is low, electronics 92 reduces the dynamic range of the background signal sensed by detector 90 and enhances the sensitivity of the technique for detecting anomalies described above.

The digital signal processor 510 may store the integrated intensity value from integrator 502 and/or the peak intensity value from detector 504 from a prior scan line for modulating the intensity of beam 38 for scanning a subsequent scan line. The digital signal processor 510 may also store other reference data (e.g. average intensity values for a number of prior scans) for comparison with the integrated value from integrator 502 and/or the peak value from detector 504 for generating the control signal to attenuator 512. While in the preferred embodiment, an AOD is used for generating the scanning beam, the above described observation applies to inspection systems employing other means for generating the scanning optical beam. While in the preferred embodiment, both the integrated and peak intensities are employed for generating the control signal for modifying the intensity of beam 38, the use of only one of the two (the peak intensity and the integrated intensity) may be adequate for some applications. Instead of using the peak intensity or the integrated intensity, an average intensity may also be used in the place of or in addition to the other two parameters.

FIG. 20 is a block diagram of a system for correcting misregistration errors by means of residual minimization and adaptive illumination. Where the variations in reflectivity of the surface to be inspected is either insignificant or where such variations have been compensated for by adaptive illumination in the manner described above in reference to FIG. 19, the data samples may no longer need to be first normalized in the manner described above in reference to FIG. 15. In such event, the system of FIG. 15 may be simplified by removing the functional blocks 362–368 related to normalization. Similarly, the functional blocks 262, 264, 266, 268 of FIG. 11, blocks 312–318 of FIG. 12 and blocks 412–418 of FIG. 17 may also be omitted in the same way in such circumstances.

While the invention has been described above by reference to different embodiments, it will be understood that different modifications and changes may be made without departing from the scope of the invention which is to be defined only by the appended claims and their equivalents.

What is claimed is:

1. A method for correcting misregistration errors in a system for detecting anomalies in a specimen such as a semiconductor wafer, said system illuminating a surface of the specimen at a two-dimensional array of locations in rows and columns; said method comprising the steps of:

generating a two-dimensional array of data samples in rows and columns, each data sample representing light modified by the specimen at a corresponding location in the two-dimensional array of locations of the sample;

defining one-dimensional groups of data samples, and each group of data samples or portion thereof defining a vector;

for at least one vector, providing a reference vector that is an average of selected vectors of data samples; and processing the at least one vector and the reference vector to correct for misregistration.

2. The method of claim 1, said defining step defining each group of data samples to be a row of data samples.

3. The method of claim 2, said providing step providing said reference vector by computing a weighted average of said selected vectors.

4. The method of claim 2, said processing step being performed on data samples within a window along said at least one vector, said window containing the same or fewer number of data samples than the at least one vector.

5. The method of claim 4, said at least one vector having a number of data samples, said number being in the range of about 512 to 8192.

6. The method of claim 1, said processing step comprising processing different sets of data samples of said reference vector, or signals derived therefrom, wherein at least some data samples in such sets are offset from the data samples of the at least one vector.

7. The method of claim 6, said defining step defining each group of data samples to be a row of data samples, wherein at least one of the sets of data samples of the reference vector is offset by one or more columns relative to the data samples in the at least one vector.

8. The method of claim 6, wherein the processing step comprises crosscorrelating each set of data samples of said reference vector with said at least one vector to obtain a crosscorrelation coefficient corresponding to each of the sets.

9. The method of claim 8, wherein the processing step derives a maximum value of the correlation coefficient for each data sample in the at least one vector.

10. The method of claim 9, further comprising re-positioning each of at least some data samples of the at least one vector so that it is identified by the location, in the two-dimensional array of data samples, of the corresponding data sample in the set of data samples in the reference vector for which the corresponding crosscorrelation coefficient is maximum.

11. The method of claim 6, wherein the processing step comprises computing a residual value between each set of data samples of said reference vector and said at least one vector.

12. The method of claim 11, further comprising comparing the residual values to obtain an offset value corresponding to a minimum residual value.

13. The method of claim 11, further comprising normalizing the data samples of said reference vector and of the at least one vector prior to the computing step, wherein the computing step computes a sum of differences between data samples of each of said sets of said normalized reference vector and the data samples of said normalized at least one vector.

14. The method of claim 2, said obtaining step deriving the reference vector from selected vectors comprising data samples that are in different rows but the same columns in the two-dimensional array of data samples.

15. The method of claim 14, said providing step providing a reference vector $G_{i,j}$ given by:

$$G_{i,j} = \sum_{q=-H/2}^{H/2-1} D_q Y_{(i+q),j}$$

where $Y_{i,j}$ is the data sample value at the ith row, jth column of the two-dimensional array;

$D_q$ are weighting coefficients;

H is the number of said selected vectors for generation of the reference vector;

$G_{i,j}$ is the value of the reference vector at the ith row jth column of the two-dimensional array;

where j ranges from $(N/2-1)$ to $-N/2$ so that the at least one vector, reference vector and selected vectors each has N data samples.

16. The method of claim 15, said processing step including crosscorrelating selected data samples of the at least one vector with selected sets of data samples of the reference vector according to the following equations:

$$\overline{Y}_{i,j} = \frac{1}{A} \sum_{p=-A/2}^{A/2-1} Y_{i,(j+p)}$$

$$\overline{G}_{i,j} = \frac{1}{A} \sum_{p=-A/2}^{A/2-1} G_{i,(j+p)}$$

where

A is a size of a window within which averaging is performed; and $\overline{Y}_{i,j}$, $\overline{G}_{i,j}$ are the averaged values of $Y_{i,j}$, $G_{i,j}$ within the window of width A;

$$C_{i,j}(m) = \frac{\sum_{l=-W/2}^{W/2-1} (G_{i,(j+l+m)} - \overline{G}_{i,(j+l+m)})(\overline{Y}_{i,(j+l)} - Y_{i,(j+l)})}{\sqrt{\sum_{l=-W/2}^{W/2-1} (G_{i,(j+l+m)} - \overline{G}_{i,(j+l+m)})^2} \sqrt{\sum_{l=-W/2}^{W/2-1} (Y_{i,(j+l)} - \overline{Y}_{(i,j+l)})^2}}$$

where $C_{i,j}(m)$ is a crosscorrelation coefficient at the ith row and jth column when the reference vector is in the same row but offset by m data samples relative to the at least one vector; and W is a size of a correlation window for the crosscorrelation coefficient.

17. The method of claim 16, wherein W includes a number of data samples, said number being in the range of about 4 to 64.

18. The method of claim 2, said generating step generating sequentially rows of said data samples and the at least one vector and the reference vector, wherein said providing step comprises causing a relative time delay between a set of data samples of the reference vector and selected data samples of the at least one vector.

19. The method of claim 2, further comprising repeating the providing and processing steps for a plurality of different vectors in the two-dimensional array.

20. The method of claim 19, wherein at least two of the plurality of vectors are in the same row and are each shorter than the row.

21. The method of claim 19, wherein the processing step re-positions at least some data samples in each of at least some of the plurality of vectors in the two-dimensional array so that it is identified by the location, in the two-dimensional array of data samples, of a corresponding set of data samples in the reference vector, and derives at least one reference vector from one or more re-positioned vectors when the providing and processing steps are repeated in a recursive operation.

22. The method of claim 19, wherein the processing step re-positions at least some data samples in each of at least some of the plurality of vectors in the two-dimensional array so that it is identified by the location, in the two-dimensional array of data samples, of a corresponding set of data samples of the reference vector, wherein the processing step derives a reference vector from one or more vectors that have not been re-positioned when the providing and processing steps are repeated in a non-recursive operation.

23. The method of claim 1, wherein the processing step compares at least some data samples of the at least one vector and those of the reference vector to select data samples of the reference vector that best match the those of the at least some data samples of the at least one vector according to a criterion and the offset there between, said method further comprising re-positioning said at least some data samples in the at least one vector according to said offset.

24. The method of claim 23, further comprising repeating the providing, processing and re-positioning steps for a plurality of different vectors in the two-dimensional array.

25. The method of claim 2, said system illuminating the surface of the specimen by scanning a light beam along the rows of locations, wherein said generating step generates the data samples by detecting light scattered or reflected by the surface.

26. The method of claim 25, said method further comprising detecting the light scattered or reflected by the surface and modifying intensity of the light beam in response to the scattered or reflected light that is detected.

27. The method of claim 25, said detecting step including increasing contrast from any pattern on the surface of the specimen.

28. The method of claim 25, said light beam having a point spread function, wherein said providing step provides said reference vector by computing a weighted average of vectors with weights that are functions of the point spread function of the light beam.

29. The method of claim 2, further comprising collecting intensity values related to light modified by the specimen at a plurality of sites, wherein said generating step includes interpolating said intensity values to obtain said two-dimensional array of data samples.

30. A method for correcting misregistration errors in a system for detecting anomalies in a specimen such as a semiconductor wafer, said system illuminating a surface of the specimen at a two-dimensional array of locations in rows and columns; said method comprising the steps of:

generating a two-dimensional array of data samples in rows and columns, each data sample in a row and column representing light modified by the specimen at a corresponding location in the two-dimensional array of locations;

comparing the data samples of a target subarray and the data samples of each of a plurality of reference subarrays, or between signals derived therefrom, the target and the reference subarrays having the same dimensions, one of the reference subarrays being at a reference position and the remaining reference subarrays being offset from the reference position by at least one row and/or column of data samples to select a pair of offset values; and repositioning the target subarray according to the pair of offset values.

31. The method of claim 30, said comparing step including computing a residual value between the data samples of a target subarray and the data samples of each of a plurality of reference subarrays, or between signals derived therfrom, to obtain a plurality of residual values each corresponding to one of said plurality of reference subarrays.

32. The method of claim 31, said comparing step including determining a pair of offset values corresponding to a minimum residual value, said re-positioning step repositioning the target subarray according to such pair of offset values.

33. The method of claim 31, said computing step also including deriving a normalized target subarray from said target subarray and deriving a plurality of normalized reference subarrays from said plurality of reference subarrays, wherein the residual values are obtained by calculating the residual value between the normalized target subarray and each of the plurality of normalized reference subarrays.

34. The method of claim 33, said deriving step including calculating, for each of at least some of the data samples in the target subarray and/or reference subarrays, a corresponding average value of data samples.

35. The method of claim 34, said deriving step including dividing each of at least some of such data samples or signals derived therefrom in a target or reference subarray by its corresponding average value to obtain said normalized target or reference subarray.

36. The method of claim 35, said deriving step including subtracting from each of at least some of such data samples in a target or reference subarray a fraction of its corresponding average value to obtain a difference and dividing such difference by its corresponding average value to obtain said normalized target or reference subarray.

37. The method of claim 35, said calculating step calculating the corresponding average value of data samples that is a weighted average of data samples.

38. The method of claim 37, wherein said calculating step calculates, for each of at least some of the data samples in the target subarray and/or reference subarrays, a corresponding average value of data samples in a number of rows and a number of columns from such data sample.

39. The method of claim 38, said system illuminating the surface of the specimen by scanning a light beam along the rows of locations, said light beam characterized by a point spread function having a lateral extent, said data samples in said number of rows and said number of columns from which said corresponding average value is calculated are within the lateral extent of the point spread function of the light beam.

40. The method of claim 35, said deriving step deriving the normalized target subarray from said target subarray and the plurality of normalized reference subarrays from said plurality of reference subarrays according to the following equations:

$$R^N_{i,j} = \frac{R_{i,j} - \alpha_R \overline{R}_{i,j}}{\overline{R}_{i,j}}$$

$$T^N_{i,j} = \frac{T_{i,j} - \alpha_T \overline{T}_{i,j}}{\overline{T}_{i,j}}$$

$$0 \leq \alpha_R \leq 1$$

$$0 \leq \alpha_T \leq 1$$

Where
$R^N_{i,j}$, $T^N_{i,j}$ are the normalized values respectively of the data samples at the ith row and jth column of the reference and target subarrays, $R_{i,j}$, $T_{i,j}$ are the values respectively of the data samples at the ith row and jth column of the reference and target subarrays, $\alpha_T, \alpha_R$ being weighting factors, and $\overline{R}_{i,j}$, $\overline{T}_{i,j}$ are local average values of the data samples over the reference and target subarrays respectively that are given by:

$$\overline{R}_{i,j} = \frac{1}{K^2} \sum_{l=\frac{-K}{2}}^{\frac{K}{2}-1} \left( \sum_{m=\frac{-K}{2}}^{\frac{K}{2}-1} R_{(i+l),(j+m)} \right)$$

$$\overline{T}_{i,j} = \frac{1}{K^2} \sum_{l=\frac{-K}{2}}^{\frac{K}{2}-1} \left( \sum_{m=\frac{-K}{2}}^{\frac{K}{2}-1} T_{(i+l),(j+m)} \right)$$

where
K is size of an averaging window.

41. The method of claim 40, wherein said residual value is computed according to the following equation:

$$H_{n,m} \equiv \sum_{i=0}^{M-1} \sum_{j=0}^{N-1} |T^N_{(i+n),(j+m)} - R^N_{i,j}|$$

where
M is the number of data samples in each column of the reference and target subarrays;
N is the number of data samples in each row of the reference and target subarrays;
m is the number of columns by which the reference subarray is offset from the reference position, where m can be zero;
n is the number of rows by which the reference subarray is offset from the reference position, where n can be zero; and
H(n,m) is the residual value corresponding to a reference subarray that is shifted by n rows and m columns from the reference position.

42. The method of claim 30, further comprising collecting intensity values related to light modified by the specimen at a plurality of sites, wherein said generating step includes interpolating said intensity values to obtain said two-dimensional array of data samples.

43. A method for correcting misregistration errors in a system for detecting anomalies in a specimen such as a semiconductor wafer, said system illuminating a surface of the specimen at a two-dimensional array of locations in rows and columns; said method comprising the steps of:

generating a two-dimensional array of data samples in rows and columns, each data sample in a row and column representing light modified by the specimen at a corresponding location in a row and column of locations;

crosscorrelating a target subarray and each of a plurality of reference subarrays of data samples, or signals derived therefrom, to obtain a plurality of sets of crosscorrelation values, the target and the reference subarrays having the same dimensions, one of the reference subarrays being at a reference position and the remaining reference subarrays being offset from the reference position by at least one row and/or column of data samples; and selecting the reference subarray that corresponds to a set of crosscorrelation values according to a criterion.

44. The method of claim 43, further comprising deriving a normalized target subarray from said target subarray and deriving a plurality of normalized reference subarrays from said plurality of reference subarrays, wherein the crosscorrelating step crosscorrelates the normalized target subarray and each of the plurality of normalized reference subarrays.

45. The method of claim 44, said deriving step including calculating, for each of at least some of the data samples in the target subarray and/or reference subarrays, a corresponding average value of data samples.

46. The method of claim 45, said deriving step including dividing each of at least some of such data samples or signals derived therefrom in a target or reference subarray by its corresponding average value to obtain said normalized target or reference subarray.

47. The method of claim 46, said deriving step including subtracting from each of at least some of such data samples in a target or reference subarray a fraction of its corresponding average value to obtain a difference and dividing such difference by its corresponding average value to obtain said normalized target or reference subarray.

48. The method of claim 46, said calculating step calculating the corresponding average value of data samples that is a weighted average of data samples.

49. The method of claim 48, wherein said calculating step calculates, for each of at least some of the data samples in the target subarray and/or reference subarrays, a corresponding average value of data samples in a number of rows and a number of columns from such data sample.

50. The method of claim 49, said system illuminating the surface of the specimen by scanning a light beam across the rows of locations in a raster pattern, said light beam characterized by a point spread function having a lateral extent, said data samples in said number of rows and said number of columns from which said corresponding average value is calculated are within the lateral extent of the point spread function of the light beam.

51. The method of claim 47, said deriving step deriving the normalized target subarray from said target subarray and the plurality of normalized reference subarrays from said plurality of reference subarrays according to the following equations:

$$R^N_{i,j} = \frac{R_{i,j} - \alpha_R \overline{R}_{i,j}}{\overline{R}_{i,j}}$$

$$T^N_{i,j} = \frac{T_{i,j} - \alpha_T \overline{T}_{i,j}}{\overline{T}_{i,j}}$$

$$0 \leq \alpha_T \leq 1$$
$$0 \leq \alpha_R \leq 1$$

where $R^N_{i,j}, T^N_{i,j}$ are the normalized values respectively of the data samples at the ith row and jth column of the reference and target subarrays, $R_{i,j}, T_{i,j}$ are the values respectively of the data samples at the ith row and jth column of the reference and target subarrays, $\alpha_T, \alpha_R$ being weighting factors, and $\overline{R}_{i,j}, \overline{T}_{i,j}$ are local average values for the ith row and jth column of the data samples over the reference and target subarrays respectively that are given by:

$$\overline{R}_{i,j} = \frac{1}{K^2} \sum_{l=\frac{-K}{2}}^{\frac{K}{2}-1} \left( \sum_{m=\frac{-K}{2}}^{\frac{K}{2}-1} R_{(i+l),(j+m)} \right)$$

$$\overline{T}_{i,j} = \frac{1}{K^2} \sum_{l=\frac{-K}{2}}^{\frac{K}{2}-1} \left( \sum_{m=\frac{-K}{2}}^{\frac{K}{2}-1} T_{(i+l),(j+m)} \right)$$

where

K is size of an averaging window.

52. The method of claim 51, wherein said crosscorrelation values are computed according to the following equation:

$$C_{i,j}(n,m) = \frac{\sum_{o=-\frac{V}{2}}^{\frac{V}{2}-1} \sum_{p=-\frac{W}{2}}^{\frac{W}{2}-1} T^N_{(i+n+o),(j+m+p)} R^N_{(i+o),(j+p)}}{\sqrt{\sum_{o=-\frac{V}{2}}^{\frac{V}{2}-1} \sum_{p=-\frac{W}{2}}^{\frac{W}{2}-1} \{T^N_{(i+n+o),(j+m+p)}\}^2} \sqrt{\sum_{o=-\frac{V}{2}}^{\frac{V}{2}-1} \sum_{p=-\frac{W}{2}}^{\frac{W}{2}-1} \{R^N_{(i+o),(j+p)}\}^2}}$$

where

W is the crosscorrelation window in the ±Y direction and V is the crosscorrelation window in the ±X direction;

where m is the number of columns offset from the reference position;

n is the number of rows offset from the reference position; and $C_{i,j}(n,m)$ is a correlation coefficient at data sample position (i,j) at offsets n, m.

53. The method of claim 43, said selecting step selecting the reference subarray that corresponds to a maximum set of crosscorrelation values.

54. The method of claim 43, further comprising collecting intensity values related to light modified by the specimen at a plurality of sites, wherein said generating step includes interpolating said intensity values to obtain said two-dimensional array of data samples.

55. A method for detecting anomalies in the specimen such as a semiconductor wafer, said method comprising the steps of:

scanning a light beam across the specimen along scan lines;

detecting light originating from the light beam after such light has been modified by the specimen for detecting anomalies in the specimen; and controlling intensity of the light beam as a function of reference data to correct for variations in the detected light caused by optical characteristics of the specimen apart from the anomalies.

56. The method of claim 55, further comprising storing signals representative of light that is detected in the detecting step, said controlling step controlling intensity of the light beam as a function of said stored signals.

57. The method of claim 55, said detecting step detecting a peak value and/or an integrated or average value of the intensity of the light modified by the specimen along a first scan line, said controlling step controlling intensity of the light beam in response to light detected in the detecting step for scanning a second scan line according to the peak value and/or the integrated or average value of the intensity of the light modified by the specimen along the first scan line.

58. The method of claim 55, said scanning step employing an acousto-optic deflector, said controlling step applying to the acousto-optic deflector a signal that is a function of the data.

59. An apparatus for detecting anomalies in the specimen such as a semiconductor wafer, comprising:

means for scanning a light beam across the specimen along scan lines;

a detector device detecting light originating from the light beam after such light has been modified by the specimen for detecting anomalies in the specimen; and means for controlling intensity of the light beam as a function of reference data to correct for variations in the detected light caused by optical characteristics of the specimen apart from the anomalies.

60. The apparatus of claim 59, further comprising a storage storing signals representative of light that is detected by the detector device, said controlling means controlling intensity of the light beam as a function of said stored signals.

61. The apparatus of claim 59, said detector device detecting a peak value and/or an integrated or average value of the intensity of the light modified by the specimen along a first scan line, said controlling means controlling intensity of the light beam in response to light detected by the detector device for scanning a second scan line according to the peak value and/or the integrated or average value of the intensity of the light modified by the specimen along the first scan line.

62. The apparatus of claim 59, said scanning means including an acousto-optic deflector, said controlling means applying to the acousto-optic deflector a signal that is a function of the data.

63. An apparatus for correcting misregistration errors in a system for detecting anomalies in a specimen such as a semiconductor wafer, said system illuminating a surface of the specimen at a two-dimensional array of locations in rows and columns; said apparatus comprising:

means for generating a two-dimensional array of data samples in rows and columns, each data sample representing light modified by the specimen at a corresponding location in the two-dimensional array of locations of the data sample;

means for defining one-dimensional groups of data samples, each group of data samples or portion thereof defining a vector;

means for providing a reference vector that is an average of selected vectors of data samples for at least one vector in the two-dimensional array; and means for processing the at least one vector and the reference vector to correct for misregistration.

64. The apparatus of claim 63, said defining means comprising means for defining each group of data samples to be a row of data samples.

65. The apparatus of claim 64, wherein said generating means generates the rows of data samples sequentially, said processing means comprising:

two signal processing paths for processing the rows of data samples; and time delay means for introducing a time delay between the two signal processing paths in order to cause a time shift between the reference vector and the at least one vector.

66. The apparatus of claim 64, said processing means processing said at least one vector and a plurality of sets of data samples of the reference vector to obtain a plurality of offset values, said time delay means introducing different time delays between the two signal processing paths in order to generate said plurality of sets of data samples of the reference vector.

67. An apparatus for correcting misregistration errors in a system for detecting anomalies in a specimen such as a semiconductor wafer, said system illuminating a surface of the specimen at a two-dimensional array of locations in rows and columns; said apparatus comprising:

means for generating a two-dimensional array of data samples in rows and columns, each data sample in a row and column representing light modified by the specimen at a corresponding location in the row and column of locations;

means for comparing the data samples of a target subarray and the data samples of each of a plurality of reference subarrays, or between signals derived therefrom, the target and the reference subarrays having the same dimensions, one of the reference subarrays being at a reference position and the remaining reference subarrays being offset from the reference position by at least one row and/or column of data samples to select a pair of offset values; and means for repositioning the target subarray according to the pair of offset values.

68. The apparatus of claim 67, said comparing means including means for computing a residual value between the data samples of a target subarray and the data samples of each of a plurality of reference subarrays, or between signals derived therefrom, to obtain a plurality of residual values each corresponding to one of said plurality of reference subarrays.

69. The apparatus of claim 68, wherein said generating means generates the rows of data samples sequentially, said computing means comprising:

two signal processing paths for processing the rows of data samples; and time delay means for introducing a time delay between the two signal processing paths in order to generate the reference subarrays.

70. An apparatus for correcting misregistration errors in a system for detecting anomalies in a specimen such as a semiconductor wafer, said system illuminating a surface of the specimen at a two-dimensional array of locations in rows and columns; said apparatus comprising:

means for generating a two-dimensional array of data samples in rows and columns, each data sample in a row and column representing light modified by the specimen at a corresponding location in a row and column of locations;

means for crosscorrelating a target subarray and each of a plurality of reference subarrays of data, or signals derived therefrom, to obtain a plurality of sets of crosscorrelation values, the target and the reference subarrays having the same dimensions, one of the reference subarrays being at a reference position and the remaining reference subarrays being offset from the reference position by at least one row and/or column of data samples; and means for selecting the reference subarray that corresponds to a set of crosscorrelation values according to a criterion.

* * * * *